(12) United States Patent
Cheng et al.

(10) Patent No.: US 7,247,467 B2
(45) Date of Patent: Jul. 24, 2007

(54) BROAD HOST RANGE PBBR1-BASED PLASMID MUTANT DERIVATIVES HAVING ALTERED PLASMID COPY NUMBER

(75) Inventors: Qiong Cheng, Wilmington, DE (US); Luan Tao, Claymont, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 141 days.

(21) Appl. No.: 10/940,052

(22) Filed: Sep. 14, 2004

(65) Prior Publication Data
US 2005/0130307 A1 Jun. 16, 2005

Related U.S. Application Data

(60) Provisional application No. 60/503,855, filed on Sep. 17, 2003.

(51) Int. Cl.
*C12N 1/21* (2006.01)
(52) U.S. Cl. ................... 435/252.3; 435/320.1; 536/24.1
(58) Field of Classification Search .............. 435/6, 435/320.1, 325
See application file for complete search history.

(56) References Cited

U.S. PATENT DOCUMENTS

2003/0219901 A1* 11/2003 Bramucci .................... 435/476
2004/0191863 A1* 9/2004 Cheng et al. .............. 435/69.1

FOREIGN PATENT DOCUMENTS

FR   2 690 459   10/1993

OTHER PUBLICATIONS

Accession No. AAS17123 Mar. 12, 2002.*
Accession No. X66730 Mar. 1999.*
Donald R. Helinski et al., Neidhart, F.C. eds., *Escerichia coli* and *Salmonella*, vol. 2, American Society of Microbiology: Washington, D.C., pp. 2295-2324, 1996.
M. E. Kovach et al., pBBR1MCS: A Broad-Host-Range Cloning Vector, Biotechniques, vol. 16(5):800-802, 1994.
Dhruba K. Chattoraj et al., Replication Control of Plasmid P1 and Its Host Chromosome: The Common Ground, Nucleic Acid Research, vol. 57:145-186, 1997.
Maddalena V. Coppi et al., Development of a Genetic System for Geobacter sulfurreducens, Applied and Environmental Microbiology, vol. 67(7):3180-3187, 2001.
Matthew D. Lefebre et al., Construction and Evaluation of Plasmid Vectors Optimized for Constitutive and Regulated Gene Expression in Burkholderia cepacia Complex Isolates, Applied and Environmental Microbiology, vol. 68(12):5958-5984, 2002.
Michael E. Kovach et al., Four new derivatives of the broad-host-range cloning vector pBBR1MCS, carrying different antibiotic-resistance cassettes, Gene, vol. 166:175-176, 1995.
National Center for Biotechnology Information General Indentifier No. 3451546, Accession No. Y14439, Mar. 10, 2001, C. Y. Szpirer et al., Study of the mobilization and maintenance elements of the pBHR1 broad host range cloning vector.
Christian Ewering et al., Identification of novel sulfur-containing bacterial polyesters: biosynthesis of poly(3-hydroxy-S-propyl-w-thioalkanotes) containing thioether linkages in the side chains, Microbiology, vol. 148:1397-1406, 2002.
Ramesh Vemulapalli et al., Overexpression of Protective Antigen as a Novel Approach to Enchance Vaccine Efficacy of Brucella abortus Strain RB51, Infection and Immunity, vol. 68(6):3286-3289, 2000.
Gloria Del Solar et al., Molecular Microbiology, Plasmid copy number control: an ever-growing story, vol. 37(3):492-500, 2000.
Dhruba K. Chattoraj, Control of plasmid DNA replication by iterons: no longer paradoxical, Molecular Microbiology, vol. 37(3):467-476, 2000.
Jorg Overhage et al., Biotransformation of Eugenol to Ferulic Acid by a Recombinant Strain of Ralstonia eutropha H16, Applied and Environmental Microbiology, vol. 68(9):4315-4321, 2002.
Humberto J. O. Ramos et al., Monitoring Azospirillum-wheat interactions using the gfp and gusA genes constitutively expressed from a new broad-host range vector, Journal of Biotechnology, vol. 97:243-252, 2002.
Thomas J. Schmidhauser et al., Regions of Broad-Host-Range Plasmid RK2 Involved in Replication and Stable Maintenance in Nine Species of Gram-Negative Bacteria, Journal of Bacteriology, vol. 164(1):446-455, 1985.
Hongsheng Su et al., Development of a genetic system for the transfer of DNA into Flavobacterium heparinum, Microbiology, vol. 147:581-589, 2001.
Rudy Antoine et al., Isoloation and molecular characterization of a novel broad-host-range plasmid from *Bordetella bronchispetica* with sequence similarities to plasmids from Gram-positive organisms, Molecular Microbiology, vol. 6(13):1785-1799, 1992.
Rojana Sukchawalit et al., Construction and characterization of regulated L-arabinose-inducible broad host range expression vectors in Xanthomonas, FEMS Microbiology Letters, vol. 181:217-223, 1999.
Cedric Y. Szpirer et al., Mobilization Function of the pBHR1 Plasmid, a Derivative of the Broad-Host-Range Plasmid pBBR1, Journal of Bacteriology, vol. 183(6):2101-2110, 2001.
Cedric Y. Szpirer et al., Interaction between the RP4 coupling protein TraG and the pBHR1 mobilization protein Mob, Molecular Microbiology, vol. 37(6):1283-1292, 2000.

* cited by examiner

*Primary Examiner*—James Ketter

(57) ABSTRACT

The present invention describes a mutant plasmid replication control region having the ability to convey a phenotype of altered plasmid copy number to the plasmid on which it resides. The mutant replication control region is based on a similar region isolated from the pBBR1 plasmid family. Plasmids containing this replication control region cannot be classed as belonging to any known incompatibility group and thus may co-exist with a broad range of other plasmids in a single host.

15 Claims, 4 Drawing Sheets

Figure 3

Figure 1:
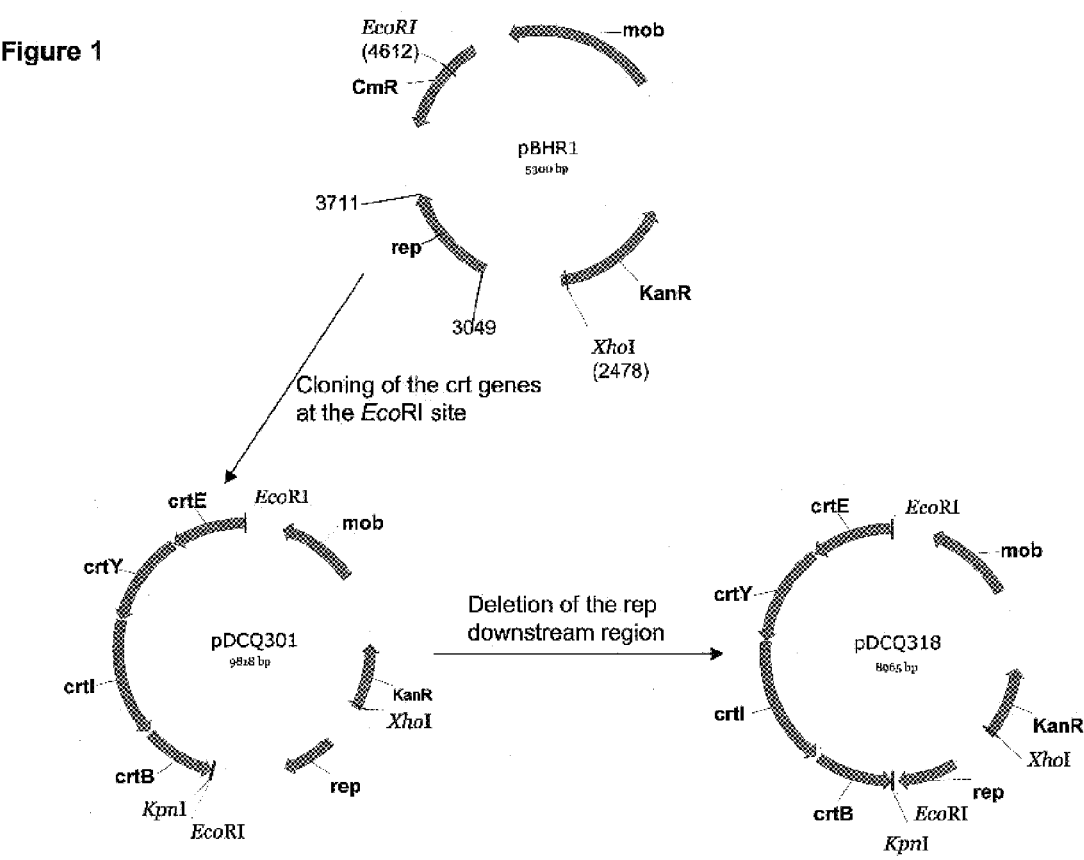

```
                           2478                3049                          3711  3765
pDCQ318                                         ▓▓▓▓▓▓▓▓▓▓▓▓▓▓▓▓▓▓▓▓▓▓▓▓▓▓▶

T3262G  T3344C
pDCQ318M1                                        ▓▓▓▓▓▓|▓▓▓▓|▓▓▓▓▓▓▓▓▓▓▓▶
                                                             C3347T
pDCQ318M2                                         ▓▓▓▓▓▓▓▓▓|▓▓▓▓▓▓▓▓▓▓▓▶

C2496T C2634del T2805C                C3269T        T3604C
pDCQ318M3          |      |      |              ▓▓▓|▓▓▓▓▓▓▓▓▓▓▓▓|▓▓▓▓▶

T2663C A2771G    C3003T
pDCQ318M4                |      |        |▓▓▓▓▓▓▓▓▓▓▓▓▓▓▓▓▓▓▓▓▓▓▶

C2634del                 G3165A  C3347T
pDCQ318M5                  |                    ▓▓|▓▓▓▓|▓▓▓▓▓▓▓▓▓▓▶

C2633del C2634del                   C3347T           A3729G
pDCQ318M7                 |                     ▓▓▓▓▓▓▓▓|▓▓▓▓▓▓▓▓▓▓▓▓▶  |

C3003T
pDCQ318M8                                |▓▓▓▓▓▓▓▓▓▓▓▓▓▓▓▓▓▓▓▓▓▓▶

T2914C T2935C          C3347T    A3570G A3641C
pDCQ318M14                    ||                ▓▓|▓▓▓▓▓|▓▓▓▓▓▓▓|▓▓|▶

T2579C
                 G2490A  C2634del C2838A C3003T            G3456A         T3739A
pDCQ318M32         |  |   |       |       |▓▓▓▓▓▓▓▓▓▓|▓▓▓▓▓▓▓▓▓▶  |

C3003T G3165A       T3468C          T3747C
pDCQ318M35                           |▓▓▓|▓▓▓▓▓▓▓|▓▓▓▓▓▓▓▓▓▶ |
```

BROAD HOST RANGE PBBR1-BASED PLASMID MUTANT DERIVATIVES HAVING ALTERED PLASMID COPY NUMBER

This application claims the benefit of U.S. Provisional Application No. 60/503,855 filed Sep. 17, 2003.

FIELD OF INVENTION

The present invention relates to the field of molecular biology and cloning vectors. More specifically, the present invention relates to broad host range plasmids derived from pBBR1 having altered plasmid copy number.

BACKGROUND OF THE INVENTION

The creation of a recombinant host suitable for high-level production of a specific product typically requires significant metabolic engineering to the native host machinery and biosynthetic pathways. In response to needs for high-level gene expression, many specialized expression vectors have been created by manipulating a number of different genetic elements that control aspects of transcription, translation, protein stability, oxygen limitation, and secretion from the host cell. More specifically, the molecular features that must be considered when designing systems for optimal gene expression include: 1.) the nature of the relevant transcriptional promoter and terminator sequences; 2.) the strength of the ribosome binding site; 3.) the final cellular location of the synthesized foreign protein; 4.) the efficiency of translation in the host organism; 5.) the intrinsic stability of the cloned gene protein within the host cell; 6.) the codon usage within the cloned gene, such that its frequency approaches the frequency of preferred codon usage of the host cell; and 7.) the number of copies of the cloned gene and whether the gene is plasmid-borne or integrated into the genome of the host cell.

Although each of the modifications described above has tremendous utility, the ease of testing each modification in a particular host organism for production of a specific protein product as a means to increase gene expression varies widely. For example, modification of the codon usage of a particular cloned gene is a tedious process, requiring nucleotide base pair modifications throughout the gene of interest. In contrast, one of the easiest means to increase gene expression involves increasing the number of copies of the plasmid-borne cloned gene(s), either by: 1.) increasing the number of copies of the cloned gene within each expression plasmid; or 2.) increasing the copy number of the plasmid on which the gene to be expressed resides. The former requires additional cloning for each gene that is to be expressed within a particular expression plasmid and multiple copies of an identical gene may be unstable due to homologous recombination. The latter method requires synthesis of a suite of modified expression plasmids having altered plasmid copy number suitable for the particular host organism of interest; however, numerous different cloned genes can readily be tested within this suite of plasmids to determine the optimal ratio of gene copy number to gene expression level.

Concerning plasmid copy number; it is known that plasmids must control their replication so that the copy number (N) of a given plasmid within a population of cells is usually maintained within a narrow Gaussian distribution within a given host and under defined growth conditions. This is required, since plasmids must co-exist stably within their hosts and minimize metabolic load upon the cell. Specifically, over-accumulation of plasmid copies within a cell can slow cell growth and eventually cause cell death. In contrast, a plasmid replication rate that is too slow can lead to plasmid-free cells, since plasmid-free cells often grow faster and can outnumber plasmid-carrying cells in the population. Means for regulating plasmid copy number are the result of an autoregulatory control mechanism, wherein the plasmid DNA concentration itself determines the rate at which new plasmid copies are generated. In general, the initiation of plasmid replication may be controlled by regulating the amount of available primer for the initiation of DNA replication, regulating the amount of essential replication proteins, or regulating the function of essential replication proteins. Several recent reviews discuss details concerning plasmid copy number control (see, for example, Helinski, D. R., et al. Replication control and other stable maintenance mechanisms of plasmids. In *Escherichia coli* and *Salmonella*, Vol. 2. Neidhardt, F. C., et al. Eds. American Society of Microbiology: Washington, D.C., pp. 2295–2324 (1996); Chattoraj, D. K. and Schneider, T. D., *Prog Nucleic Acid Res Mol Biol*, 57:145–186 (1997); del Solar, G. & Espinosa, M., *Mol Microbiol*, 37(3): 492–500 (2000); and Chattoraj, D. K., *Mol Microbiol*, 37(3):467–476 (2000)).

A second consideration when selecting a particular expression vector is the host range of the vector itself. Specifically, host range refers to the types of microbes in which a plasmid will replicate. One may develop a specific vector for each microbial species of interest; or, one may take advantage of available broad host range replicons that have the ability to be maintained in a wide range of microbes that are unrelated. These broad host range plasmids typically encode all of their own proteins required for replication and which function in multiple hosts. Thus, these plasmids are not dependent on their host cell. In contrast, narrow host range replicons may lack replication or segregation proficiencies (as compared to an inability to be introduced into or express genetic markers in a distantly related host), which result in their replication only in closely related species (Schmidhauser, T. J. and D. R. Helinski., *J. Bacteriol.*, 164:446–455 (1985)).

Most broad host range plasmids are classified on the basis of their intrinsic properties, according to their "incompatibility groups". This classification reflects the similarities in sequence, function, and the nature of the replicon (as replicons of the same type are unable to co-exist in a cell, while replicons from different incompatibility groups (e.g., "Inc" groups) may exist simultaneously in a single cell). Natural plasmid isolates of Gram-negative bacteria that belong to Inc groups C, N, P, Q, and W display replication and maintenance proficiency in a diversity of bacterial species.

The pBBR1 plasmid is a 2.6 kB broad host range plasmid isolated from the Gram-negative bacterium *Bordetella bronchiseptica* S87 (Antoine, R. and C. Locht, *Mol. Microbiol.*, 6(13):1785–1799 (1992); FR 2,690,459). Many derivatives of pBBR1 have been constructed to add various multiple cloning sites (Kovach et al., *Biotechniques*, 16: 800–802 (1994)), antibiotic resistance markers (Kovach et al., *Gene*, 166: 175–176 (1995)), reporter genes (Ramos et al., *J Biotechnol*, 97: 243–252 (2002)), and regulated promoters (Lefebre and Valvano, *Appl Environ Microbiol*, 68: 5956–5964 (2002); Sukchawalit et al., *FEMS Microbiol Lett*, 181: 217–223 (1999)). These pBBR1-based plasmid derivatives have been used in a variety of applications including: 1.) development of a genetic system for bacteria (Coppi et al., *Appl Environ Microbiol*, 67: 3180–3187 (2001); Su et al., *Microbiology*, 147: 581–589 (2001)); 2.) synthesis of novel polyhydroxy alkanoates (Ewering et al.,

*Microbiology,* 148: 1397–1406 (2002)); 3.) production of biocatalysts for biotransformation (Overhage et al., *Appl Environ Microbiol,* 68: 4315–4321 (2002)); and 4.) overexpression of a protective antigen to enhance vaccine efficacy (Vemulapalli et al., *Infect Immun,* 68: 3286–3289 (2000)).

One particular derivative of pBBR1 having utility as an expression/cloning vector with very broad host range maintenance is the commercially available pBHR1 (MoBiTec; Göttingen, Germany; GenBank® Y14439). Like pBBR1, pBHR1 does not belong to any of the common broad host range incompatibility groups and possesses a relatively high copy number. Both pBBR1 and pBHR1 plasmids possess two critical open reading frames (ORFs)—the first, known as rep, is involved in replication of the plasmid; and, the second ORF is known as mob. The mob gene, involved in mobilization, has been extensively characterized for this family of plasmids by Szpirer et al. (*Molecular Microb.* 37(6): 1283–1292 (2000); *J. Bacteriol.* 183(6): 2101–2110 (2001)). Plasmid pBHR1 also additionally has two selectable markers (i.e., kanamycin and chloramphenicol), while maintaining a relatively small size of only 5300 bp. These properties render pBHR1 an extremely useful cloning vector suitable for a wide range of Gram-negative bacteria.

One variation that would increase the utility of pBBR1 and plasmid derivatives within the pBBR1 family would be a means to increase the copy number of the plasmid. Specifically, it would be desirable to create a suite of mutants having altered plasmid copy number, since this would enable one to readily assess the relationship between gene copy number and gene expression. In general, increased plasmid copy number per cell can substantially increase the overall yield of proteins (i.e., titer) that are expressed by the plasmid within the host cell. Plasmid mutants having a phenotype of altered copy number are generated by random mutagenesis followed by screening to obtain mutants with the desired phenotype. Although the technique of generating these mutants is well understood by an artisan skilled in molecular biology, the utility and need for development of pBBR1-based plasmids having altered plasmid copy number has not previously been recognized.

The problem to be solved therefore is to develop a broad host range expression plasmid having the ability to: 1.) co-exist with a variety of other broad host range plasmids; and 2.) replicate within a given host under defined growth conditions, such that the plasmid copy number is altered relative to the native pBBR1-based plasmid.

The present problem has been solved by providing a suite of isolated plasmids derived from pBHR1 comprised of mutant replication control regions conveying a phenotype of increased plasmid copy number. The broad host range of the plasmids, and their compatibility with other known broad host range vectors, makes the plasmids of the present invention particularly attractive for plasmid-based protein expression within a variety of bacteria.

SUMMARY OF THE INVENTION

The present invention provides a mutant replication control region of a plasmid having the ability to convey altered plasmid copy number to the plasmid on which it resides. Also provided are plasmids comprising the mutant replication control region. The plasmids of the invention provide a method for efficiently modifying expression levels of heterologous genes within a host in a short period of time.

Several mutations have been identified within the replication control region of plasmid pBHR1 that create a phenotype of increased plasmid copy number. These mutations of the replication control region include, but are not limited to, those located at positions 2490, 2496, 2579, 2633, 2634, 2663, 2771, 2805, 2838, 2914, 2935, 3003, 3165, 3262, 3269, 3344, 3347, 3456, 3468, 3570, 3604, 3641, 3729, 3739, and 3747 of the nucleotide sequence of the replication control region of pBHR1 (comprising nucleotides 2478–3765 of SEQ ID NO:1).

Accordingly, the invention provides a method for the generation and isolation of a mutant plasmid replication control region conveying altered plasmid copy number, comprising:
 a) providing a plasmid comprising a replication control region derived from pBBR1;
 b) subjecting the plasmid of (a) to a mutagenic procedure wherein mutations are introduced into the replication control region of the plasmid;
 c) transforming the mutant plasmid of (b) into a suitable host cell;
 d) culturing said host cell of (c) and determining plasmid copy number;
 e) selecting at least one plasmid of (d) which has altered plasmid copy number relative to the plasmid of (a); and
 f) isolating mutant replication control regions from the plasmids of (e).

In another embodiment, the method whereby plasmid copy number is determined is selected from the group consisting of: use of a reporter construct to evaluate gene expression; estimation of plasmid DNA concentration by agarose gel analysis; real-time PCR; and Northern blot analysis. Furthermore, the altered plasmid copy number can be increased or decreased relative to the pBBR1-based plasmid of step (a).

In another embodiment, a mutant replication region is provided comprised of a nucleotide sequence as set forth in nucleotides 2478–3765 of SEQ ID NO:1 and having at least one point mutation independently selected from the group consisting of:
 a) a mutation of G to A at nucleotide 2490;
 b) a mutation of C to T at nucleotide 2496;
 c) a mutation of T to C at nucleotide 2579;
 d) a mutation by deletion of C at nucleotide 2633;
 e) a mutation by deletion of C at nucleotide 2634;
 f) a mutation of T to C at nucleotide 2663;
 g) a mutation of A to G at nucleotide 2771;
 h) a mutation of T to C at nucleotide 2805;
 i) a mutation of C to A at nucleotide 2838;
 j) a mutation of T to C at nucleotide 2914;
 k) a mutation of T to C at nucleotide 2935;
 l) a mutation of C to T at nucleotide 3003;
 m) a mutation for substitution of G to A at nucleotide 3165;
 n) a mutation of T to G at nucleotide 3262;
 o) a mutation of C to T at nucleotide 3269;
 p) a mutation of T to C at nucleotide 3344;
 q) a mutation of C to T at nucleotide 3347;
 r) a mutation for substitution of G to A at nucleotide 3456;
 s) a mutation for substitution of T to C at nucleotide 3468;
 t) a mutation for substitution of A to G at nucleotide 3570;
 u) a mutation of T to C at nucleotide 3604;
 v) a mutation of A to C at nucleotide 3641;
 w) a mutation of A to G at nucleotide 3729;
 x) a mutation of T to A at nucleotide 3739; and
 y) a mutation of T to C at nucleotide 3747.

Additionally, a further embodiment provides a mutant replication gene having the nucleotide sequence as set forth in SEQ ID NO:3 and a mutant replication gene as set forth in SEQ ID NO:3 comprising at least one point mutation independently selected from the group consisting of:

a) a mutation for substitution of G to A at nucleotide 117;
b) a mutation of T to G at nucleotide 214;
c) a mutation of C to T at nucleotide 221;
d) a mutation of T to C at nucleotide 296;
e) a mutation of C to T at nucleotide 299;
f) a mutation for substitution of G to A at nucleotide 408;
g) a mutation for substitution of T to C at nucleotide 420;
h) a mutation for substitution of A to G at nucleotide 522;
i) a mutation of T to C at nucleotide 556; and
j) a mutation of A to C at nucleotide 593.

Another embodiment relates to plasmids comprising the mutant replication control regions and/or replication genes of the invention and Gram-negative host cells comprising a mutant replication control region of the invention.

BRIEF DESCRIPTION OF FIGURES AND SEQUENCE DESCRIPTIONS

FIG. 1 is schematic diagram showing the construction of pBHR1-based reporter plasmids pDCQ301 and pDCQ318.

Figure 2:
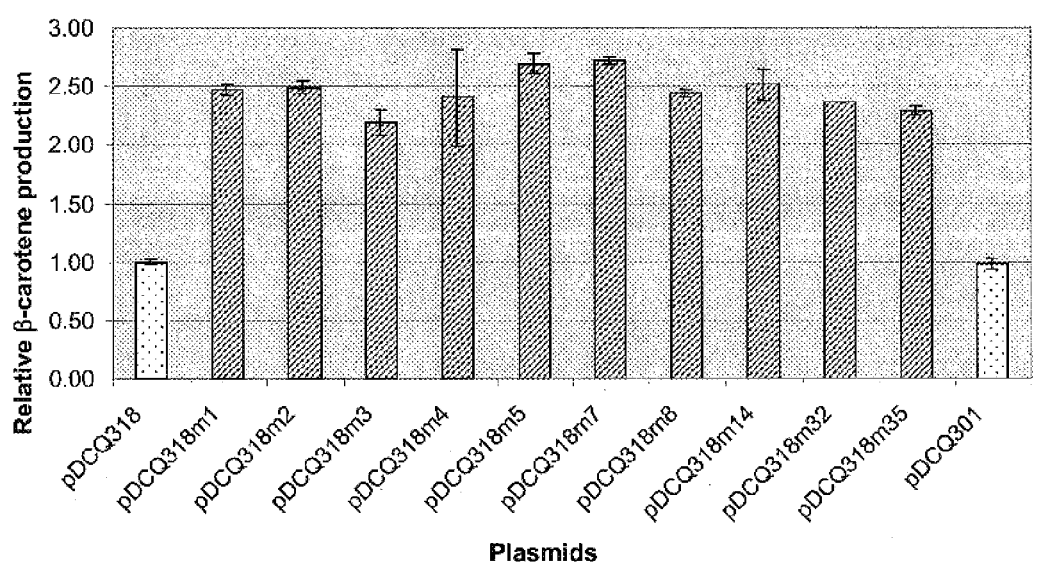

FIG. 2 provides a graphical summary of the relative β-carotene production observed in *E. coli* containing carotenoid reporter plasmids and mutant derivatives having modified replication control regions.

FIG. 3 is a summary of all mutations-created within the replication control region of pDCQ318 and its mutant derivatives (with the exception of the insertion of cytosine at nucleotide position 3030 in pDCQ318 and each of the mutant derivatives).

Figure 4:
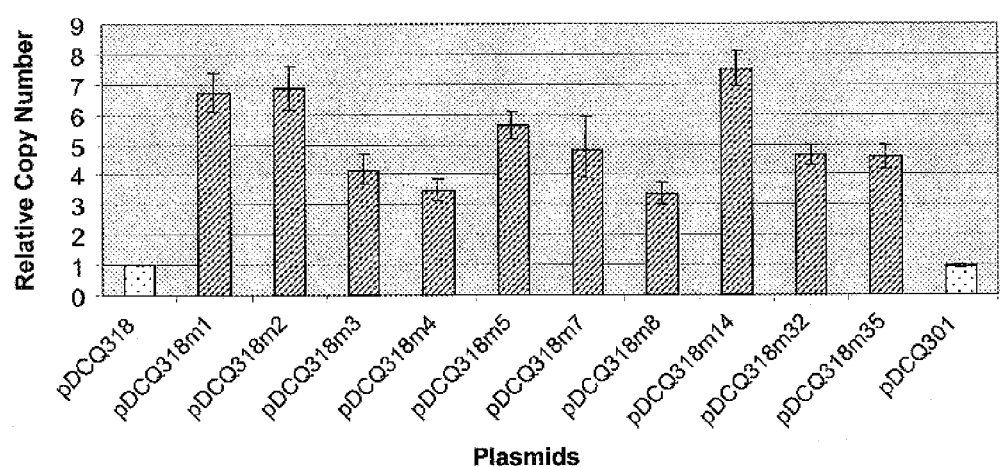

FIG. 4 provides a graphical summary of the relative plasmid copy number of pDCQ318 and its mutant derivatives, as determined by real-time PCR.

The following sequence descriptions and sequence listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the wild-type sequence of the broad host range expression plasmid pBHR1 (GenBank® Y14439). The replication control region subjected to mutagenesis in this study corresponds to nucleotides 2478–3765; the rep gene itself is located between nucleotides 3049–3711 and encodes the Rep protein (provided as SEQ ID NO:2).

SEQ ID NO:3 is the nucleotide sequence of the mutant rep gene of the invention.

SEQ ID NOs:4–21 are mutant replication control regions and Rep proteins, as identified in Table 1.

TABLE 1

Summary of Replication Control Region SEQ ID Numbers

| Replication Control Region | Nucleotide SEQ ID of replication control region | Amino Acid SEQ ID of Rep protein |
|---|---|---|
| PDCQ318 | SEQ ID NO:4 | SEQ ID NO:5 |
| PDCQ318M1 | SEQ ID NO:6 | SEQ ID NO:7 |
| PDCQ318M2 | SEQ ID NO:8 | SEQ ID NO:9 |
| PDCQ318M3 | SEQ ID NO:10 | SEQ ID NO:11 |
| PDCQ318M4 | SEQ ID NO:12 | SEQ ID NO:5 |
| PDCQ318M5 | SEQ ID NO:13 | SEQ ID NO:14 |
| PDCQ318M7 | SEQ ID NO:15 | SEQ ID NO:16 |
| PDCQ318M8 | SEQ ID NO:17 | SEQ ID NO:5 |
| PDCQ318M14 | SEQ ID NO:18 | SEQ ID NO:19 |
| PDCQ318M32 | SEQ ID NO:20 | SEQ ID NO:5 |
| PDCQ318M35 | SEQ ID NO:21 | SEQ ID NO:5 |

SEQ ID NOs:22–25 are the primers pBHRcrt_1F, pBHRcrt_1R, pBHRcrt_2F, and pBHRcrt_2R, respectively, that were used to amplify the *Pantoea stewartii* crtEYIB gene cluster for use as a reporter construct.

SEQ ID NOs:26 and 27 are the primers 301rep_F and 301rep_R, respectively, that were used to amplify the replication control region in pDCQ301.

SEQ ID NOs:28 and 29 are the primers pBHR1rep_F and 301rep_R2, respectively, that were used for error-prone PCR reactions.

SEQ ID NOs:30 and 31 are the forward and reverse primers, respectively, that were designed to amplify a 65 bp region at the 3' end of the crtE gene on target plasmid DNA.

SEQ ID NOs:32 and 33 are the forward and reverse primers, respectively, that were designed to amplify a 62 bp region of the *E. coli* 16S rRNA gene.

SEQ ID NO:34 is the 16s rRNA gene for *Methylomonas* sp. 16a.

SEQ ID NO:35 is a 2152 bp partial nucleotide sequence of pDCQ301, comprising the rep gene.

SEQ ID NO:36 is the Rep protein of pDCQ301.

The following biological deposit under the terms of the Budapest Treaty on the International Recognition of the Deposit of Microorganisms for the Purposes of Patent Procedure:

| Depositor Identification Reference | International Depository Designation | Date of Deposit |
|---|---|---|
| *Methylomonas* 16a | ATCC PTA 2402 | Aug. 22, 2000 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present invention provides a mutant replication control region conveying altered plasmid copy number to plasmids on which it resides and plasmids comprising the same. The suite of mutant plasmids so created will be particularly useful for studies that require facile modification of the level of expression of heterologous proteins cloned into the plasmid.

Definitions

In this disclosure, a number of terms and abbreviations are used. The following definitions are provided.

"Open reading frame" is abbreviated ORF.

"Polymerase chain reaction" is abbreviated PCR.

The term "plasmid copy number" refers to the average number of molecules of a plasmid contained within a cell. The copy number of a plasmid in the cell is determined by regulating the initiation of plasmid replication. In general, the initiation of plasmid replication may be controlled by regulating the amount of available primer for the initiation of DNA replication, regulating the amount of essential replication proteins, or regulating the function of essential replication proteins.

The term "altered plasmid copy number" will refer to a copy number associated with a specific plasmid in a specific host, which can be measured by an assay method, where that copy number is either greater than or less than the copy number associated with the reference plasmid. "Increased plasmid copy number" refers to an altered plasmid copy number that is greater than that associated with the reference plasmid. "Diminished plasmid copy number" is an altered plasmid copy number that is less than that associated with the reference plasmid. For the purposes herein, the plasmid copy numbers of mutant plasmids are compared relative to the non-mutagenized parent plasmid (the wild-type).

The term "Rep" refers to a replication protein encoded by a "rep" gene. The replication gene of a plasmid is responsible for the replication characteristics of the plasmid.

The term "replication control region" means a region of DNA containing a rep gene or a gene having homology to a rep gene that is responsible for controlling the replication, and affecting the plasmid copy number. Preferred replication control regions of interest in the present invention will comprise the rep gene and up to about 1 kB of flanking DNA upstream of the gene and up to about 0.2 kB of flanking DNA downstream of the gene.

Typically, replication control regions of the invention are derived from pBBR1 (Antoine, R. and C. Locht, supra). Thus, the term "replication control region derived from pBBR1" refers to a replication control region isolated from pBBR1 or any plasmid derivative within the pBBR1 plasmid family, wherein the replication control region is the same as that of pBBR1. pBHR1 (GenBank® Accession No. Y14439; commercially available through MoBiTec (Göttingen, Germany)) is an example of a plasmid derivative within the pBBR1 family. With respect to wild-type pBHR1, as defined by GenBank® Accession Number Y14439, the replication control region will herein be defined as that portion contained between nucleotides 2478–3765; the rep gene itself is located between nucleotides 3049–3711.

The term "mutant replication control region" or "mutant plasmid replication control region" refers to a replication control region that has been modified by a mutagenic procedure such that the nucleotide sequence of the mutant region is different than that of the non-mutagenized (wild-type) sequence. As described herein, the mutant replication control region comprises about 1300 bp, is derived from the pBBR1 and pBHR1 (GenBank® Accession No. Y14439) plasmids, and contains at least one mutation relative to the wild-type replication control region of pBBR1 and pBHR1. In one embodiment, the mutant replication control regions of the present invention will convey altered plasmid copy number to the plasmid on which it resides, relative to the plasmid copy number conveyed by the replication control region of a reference plasmid.

The term "pBBR1" will refer to the cryptic plasmid isolated from *Bordetella bronchiseptica* S87 (Antoine, R. and C. Locht, supra).

The term "pBBR1-based" or "plasmid derivative within the pBBR1 family" refers to any plasmid comprising the replication control region of pBBR1.

The term "pBHR1" will refer to the broad host range plasmid pBHR1, as represented by GenBank® Accession No. Y14439, and commercially available through MoBiTec. Plasmid pBHR1 is a plasmid derivative within the pBBR1 family and therefore has the same replication control region as that of pBBR1.

The term "mutant pDCQ318" will refer to any plasmid derivative of pDCQ318 possessing a mutant replication control region that conveys a phenotype of altered plasmid copy number. Preferred mutant plasmids of the present invention having an increased plasmid copy number relative to pDCQ318 are pDCQ318M1, pDCQ318M2, pDCQ318M3, pDCQ318M4, pDCQ318M5, pDCQ318M7, pDCQ318M8, pDCQ318M14, pDCQ318M32, and pDCQ318M35.

As used herein, the term "mutagenic procedure" refers to a process of subjecting a plasmid, or host cell comprising a plasmid, to various mutagenizing agents such that mutations occur within a specific region of DNA and said mutations can be recognized through screening procedures or selection procedures. Of particular interest in the present invention are mutations occurring in the replication control regions of plasmid pBBR1 and its derivatives.

The term "incompatibility", as applied to plasmids, refers to the inability of any two different plasmids to co-exist within the same host cell. Specifically, two plasmids from the same incompatibility group (i.e., "Inc group") cannot be maintained within the same cell. In contrast, plasmids from different "Inc" groups can be simultaneously maintained within the same host cell. The classification of a plasmid within a particular Inc group (e.g., Inc groups C, N, P, Q, or W) depends on similarities in sequence, function, and the nature of the replicon. Inc groups are most extensively defined for conjugative plasmids of Gram-negative bacteria.

The terms "plasmid", "vector" and "cassette" refer to an extra chromosomal element often carrying genes which are not part of the central metabolism of the cell, and usually in the form of circular, double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "$C_1$ carbon substrate" or "single carbon substrate" refers to any carbon-containing molecule that lacks a carbon-carbon bond. Non-limiting examples are methane, methanol, formaldehyde, formic acid, formate, methylated amines (e.g., mono-, di-, and tri-methyl amine), methylated thiols, and carbon dioxide.

The term "$C_1$ metabolizer" refers to a microorganism that has the ability to use a single carbon substrate as its sole source of energy and biomass. $C_1$ metabolizers will typically be methylotrophs and/or methanotrophs.

The term "$C_1$ metabolizing bacteria" refers to bacteria that have the ability to use a single carbon substrate as their sole source of energy and biomass. $C_1$ metabolizing bacteria, a subset of $C_1$ metabolizers, will typically be methylotrophs and/or methanotrophs.

The term "methylotroph" means an organism capable of oxidizing organic compounds that do not contain carbon-carbon bonds. Where the methylotroph is able to oxidize $CH_4$, the methylotroph is also a methanotroph.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas, Methylobacter, Methylococcus*, and *Methylosinus*.

The term "high growth methanotrophic bacterial strain" refers to a bacterium capable of growth with methane or methanol as the sole carbon and energy source and which possesses a functional Embden-Meyerof carbon flux pathway, resulting in a high rate of growth and yield of cell mass per gram of $C_1$ substrate metabolized (see WO 02/20728). The specific "high growth methanotrophic bacterial strain" described herein is referred to as "*Methylomonas* 16a", "16a" or "*Methylomonas* sp. 16a", which terms are used interchangeably and which refer to the *Methylomonas* strain used in the present invention.

The term "carotenoid" refers to a class of hydrocarbons having a conjugated polyene carbon skeleton formally derived from isoprene. This class of molecules include $C_{30}$ diapocarotenoids and $C_{40}$ carotenoids and their oxygenated derivatives.

"$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure (Formula I below), having a long central chain of conjugated double bonds, by (i) hydrogenation, (ii) dehydrogenation, (iii) cyclization, (iv) oxidation, (v) esterification/glycosylation, or any combination of these processes. This class also includes certain compounds that arise from rearrangements of the carbon skeleton (Formula I), or by the (formal) removal of part of this structure.

Formula I

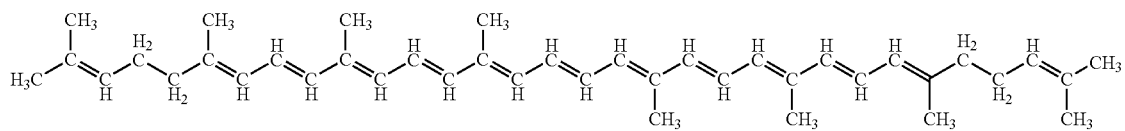

(I)

The term "ctEYIB" refers to a genetic construct comprising genes encoding: 1.) a geranylgeranyl pyrophosphate synthetase enzyme encoded by the crtE gene (which converts trans-trans-farnesyl diphosphate and isopentenyl diphosphate to pyrophosphate and geranylgeranyl diphosphate); 2.) a lycopene cyclase enzyme encoded by the crtY gene (which converts lycopene to β-carotene); 3.) a phytoene desaturase enzyme encoded by the crtI gene (which converts phytoene into lycopene via the intermediaries of phytofluene, ζ-carotene and neurosporene); and 4.) a phytoene synthase enzyme encoded by the crtB gene (which catalyzes the reaction from prephytoene diphosphate to phytoene). Together, this suite of enzymes catalyzes the conversion of phytoene to β-carotene.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of exemplary conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. In another embodiment, the stringent conditions use higher temperatures in which the washes are identical to those above except for the temperature of the final two 30 min washes in 0.2×SSC, 0.5% SDS was increased to 60° C. In a further embodiment, a set of highly stringent conditions can be used comprised of two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well-known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. In another embodiment, the minimum length for a hybridizable nucleic acid is at least about 15 nucleotides; in another embodiment at least about 20 nucleotides; and in yet a further embodiment the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as,determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humana: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*, 5:151–153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but also the characteristics of altered plasmid copy number.

"Gene" refers to a nucleic acid, fragment that expresses a specific protein, or RNA including regulatory sequences preceding (5' non-coding sequences) and following (3' non-coding sequences) the coding sequence. "Native gene" (or "wild-type gene") refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. The term "amino acid" refers to the basic chemical structural unit of a protein or polypeptide. The amino acids are identified by either one-letter code or the three-letter codes for amino acids, in conformity with the IUPAC-IYUB standards described in *Nucleic Acids Research* 13:3021–3030 (1985) and in the *Biochemical Journal* 219 (2):345–373 (1984), which are herein incorporated by reference. For a particular protein, point substitution mutations within the DNA coding region and the resulting amino acid change are specified with reference to a standard DNA and/or amino acid sequence (i.e., that of pBHR1), using one of the following notations. For example, to describe mutations in the nucleotide sequence of the replication control region, the nucleotide at the wild-type base position is first presented, followed by the specific nucleotide modification that exists in the referenced mutation, along with a reference to the specific base position wherein the mutation exists. An example of this notation is: "G to A at nucleotide 2490", wherein the wild-type nucleotide is a guanine at base pair position 2490 and the mutant nucleotide is an adenosine at that position. In contrast, to describe mutations in the amino acid sequence of the coding sequence of the Rep protein, the wild-type amino acid in three-letter abbreviation, the codon position, and the three-letter abbreviation for the mutant amino acid are provided. An example of this notation is: "Ser100 to Leu", representing mutation of the wild-type serine at codon 100 of the Rep protein to leucine in the mutant protein. It is well known in the art that alterations in a gene which result in the production of a chemically equivalent amino acid at a given site (but do not effect the functional properties of the encoded protein) are common.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the Rep protein, as set forth in SEQ ID NOs:5, 7, 9, 11, 14,16, and 19.

The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Suitable regulatory sequences" refer to nucleotide sequences located upstream (5' non-coding sequences), within, or downstream (3' non-coding sequences) of a coding sequence, and which influence the transcription, RNA processing-or stability, or translation of the associated coding sequence. Regulatory sequences may include promoters, translation leader sequences, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid fragment of the invention. Expression may also refer to translation of mRNA into a polypeptide.

"Transformation" refers to the transfer of a nucleic acid fragment into the genome of a host organism, resulting in genetically stable inheritance. As used herein, the genome of a host organism is comprised of both chromosomal and extrachromosomal genes. There are a variety of methods well known to those in the art for microbial transformation including, but not limited to: electroporation, heat shock, conjugation, biolistic bombardment, etc. Host organisms containing the transformed nucleic acid fragments are referred to as "transgenic", "recombinant" or "transformed" organisms.

The term "sequence analysis software" refers to any computer algorithm or software program that is-useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); and 4.) the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Plenum: New York, N.Y.). Within the context of this application, it will be understood that where sequence analysis software is used for analysis, that the results of the analysis will be based on the "default values" of the program referenced, unless otherwise specified. As used herein "default values" will mean any set of values or parameters set by the software manufacturer which originally load with the software when first initialized.

Standard recombinant DNA and molecular cloning techniques used herein are well known in the art and are described by Sambrook et al. (supra); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Mutagenesis of the Replication Control Region

The present invention provides a replication control region comprising approximately 1300 bp of pBHR1 (a plasmid derived from the pBBR1 plasmid family) which has been mutated to convey altered plasmid copy number to a plasmid on which it resides. The replication control region of the invention was isolated after mutagenesis of the plasmid derived from pBHR1 comprising a reporter construct (i.e., pDCQ318) and introduction of the mutagenized plasmids into a suitable host cell for screening. Although screening was performed to identify those plasmids and replication control regions conveying an increased plasmid copy number relative to the non-mutagenized parental plasmid, this should not be construed as a limitation to the invention herein. Specifically, plasmid replication control regions conveying either an increased or decreased plasmid copy number can be generated and identified, as described below.

Various methods are known for mutating a wild-type nucleotide sequence to produce a mutated product with altered activity including, but not limited to: 1.) error-prone PCR (Leung et al., *Techniques*, 1:11 –15 (1989); Zhou et al., *Nucleic Acids Res.*, 19:6052–6052 (1991); Spee et al., *Nucleic Acids Res.*, 21:777–778 (1993); Melnikov et al., *Nucleic Acids Research*, 27(4):1056–1062 (Feb. 15, 1999)); 2.) site directed mutagenesis (Coombs et al., *Proteins*, 259–311, 1 plate. Ed.: Angeletti, Ruth Hogue. Academic: San Diego, Calif. (1998)); 3.) in vivo mutagenesis; and 4.) "gene shuffling" (U.S. Pat. No. 5,605,793; U.S. Pat. No. 5,811,238; U.S. Pat. No. 5,830,721; and U.S. Pat. No. 5,837,458, hereby incorporated by reference).

Error-prone PCR is a particularly preferred method for the generation of mutations within a defined nucleotide sequence. The principal advantage of error-prone PCR is that all mutations introduced by this method will be within the replication control region, and any change may be easily controlled by changing the PCR conditions. Alternatively, in vivo mutagenesis may be employed using commercially available materials such as the *E. coli* XL1-Red strain or the *Epicurian®* *coli* XL1-Red mutator strain (Stratagene, La Jolla, Calif.; Greener and Callahan, *Strategies*, 7:32–34 (1994)). This latter strain is deficient in three of the primary DNA repair pathways (i.e., mutS, mutD, and mutT), resulting in a mutation rate 5000-fold higher than that of wild type. In vivo mutagenesis does not depend on ligation efficiency (as with error-prone PCR); however, a mutation may occur at any region of the vector and the mutation rates are generally much lower.

Alternatively, it is contemplated that a mutant replication control region with altered plasmid copy number may be constructed using the method of "gene shuffling". The method of gene shuffling is particularly attractive due to its facile implementation, and high rate of mutagenesis and ease of screening. The process of gene shuffling involves the restriction endonuclease cleavage of a nucleotide sequence (e.g., a gene) of interest into fragments of specific size in the presence of additional populations of DNA regions of both similarity to (or difference to) the sequence of interest. This pool of fragments will then be denatured and reannealed to create a mutated sequence. The mutated sequence is then screened for altered activity.

The instant microbial sequences of the present invention encoding replication control regions may be mutated and screened for altered activity by this method. The sequences should be double-stranded and can be of various lengths ranging from about 50 bp to about 10 kB. The sequences may be randomly digested into fragments ranging from about 10 bp to about 1000 bp, using restriction endonucleases well known in the art (Sambrook et al., supra). In addition to the instant microbial sequences, populations of fragments that are hybridizable to all or portions of the microbial sequence may be added. Similarly, a population of fragments that is not hybridizable to the instant sequence may also be added. Typically, these additional fragment populations are added in about a 10 to about a 20-fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. In one embodiment, the temperature is from about 80° C. to about 100° C. The nucleic acid fragments may be reannealed by cooling. In another embodiment, the temperature is from about 20° C. to about 75° C. Renaturation can be accelerated by the addition of polyethylene glycol ("PEG") or salt. A suitable salt concentration may range from 0 mM to about 200 mM. The annealed nucleic acid fragments are then incubated in the presence of a nucleic acid polymerase and dNTPs (i.e., dATP, dCTP, dGTP, and dTTP). The nucleic acid polymerase may be the Klenow fragment, Taq polymerase, or any other DNA polymerase known in the art. The polymerase may be added to the random nucleic acid fragments prior to annealing, simultaneously with annealing, or after annealing. The cycle of denaturation, renaturation and incubation in the presence of polymerase is repeated for a desired number of times. Typically, the cycle is repeated from about 2 to about 50 times, more preferably the sequence is repeated from about 10 to about 40 times. The resulting nucleic acid is a larger double-stranded polynucleotide ranging from about 50 bp to about 100 kB and may be screened for altered activity by standard cloning and expression protocols (Sambrook et al., supra).

Other well-known mutagenesis treatments include in vitro treatment with hydroxylamine (see, for example, G. O. Humpherys et al., *Molec. Gen. Genet.*, 145:101–108 (1976)), treatments of microorganisms harboring a plasmid with radiation, and mutagens used for usual mutagenesis treatments such as N-methyl-N'-nitro-N-nitrosoguanidine (NTG) and nitrous acid. For example, DNA may be exposed to a variety of agents such as radiation or chemical mutagens and then transformed into an appropriate host and screened for the desired phenotype. When creating mutations through radiation either ultraviolet (UV) or ionizing radiation may be used. Suitable short wave UV wavelengths for genetic mutations will fall within the range of 200 nm to 300 nm, where 254 nm is preferred. UV radiation in this wavelength principally causes changes within a nucleic acid sequence from guanine and cytosine to adenine and thymine. In contrast, long wave UV mutations using light in the 300 nm to 400 nm range are also possible but are generally not as effective as the short wave UV light unless used in conjunction with various activators (e.g., psoralen dyes) that interact with the DNA.

Commonly used chemical agents for mutagenic procedures include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See for example, Thomas D. Brock in Biotechnology: *A Textbook of Industrial Microbiology*, $2^{nd}$ ed. (1989) Sinauer Associates: Sunderland, Mass., or Deshpande, Mukund V., *Appl. Biochem. Biotechnol.*, 36:227 (1992), herein incorporated by reference.

Identification of Plasmids Having an Altered Plasmid Copy Number

After mutagenesis has occurred, mutants having an altered plasmid copy number may be selected by a variety of methods, including but not limited to: 1.) examination of expression levels of a reporter gene(s) present on the mutant plasmid; 2) estimation of DNA concentration change on agarose gels; 3.) real-time PCR; and 4.) Northern blot analysis. The advantages of using any of these selection methods in combination with high throughput screening techniques to rapidly assess a large population of mutants are well known to one skilled in the art and the specific methodology is well documented.

Preliminary screening for altered plasmid copy number is facile, when the mutant replication control region is present within a plasmid comprising a reporter gene(s) and wherein the plasmid is expressed within a particular host. Thus, cells containing the mutagenized replication control region are selected based on the ability to detect the over-expression or under-expression of the reporter (either directly or indirectly, by visual means or other techniques). For example, the reporter protein may be expressed alone or as a fusion to another protein. And, the reporter protein can be detected by, for example: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product), or 2.) its light-producing or modifying characteristics (e.g., the green fluorescent protein of *Aequorea victoria* fluoresces when illuminated with blue light). In the present application, β-carotene was used as the reporter molecule, since it was suitable for direct visual screen as well as quantitation based on its absorption characteristics. This molecule was synthesized as a result of the expression of the crtEYIB genes present on plasmid pDCQ318 and its derivatives. Using these means, the over-expression of the reporter was indicative of a plasmid carrying a mutagenized replication control region, wherein the replication control region was conveying a phenotype of increased plasmid copy number relative to the wild-type replication control region.

Where more quantitative means are desired to detect altered plasmid copy number, it is useful to quantify plasmid DNA in the cell. One suitable method is the use of real-time PCR (for a general review of real-time PCR applications, see Ginzinger, D. J., *Experimental Hematology*, 30:503–512 (2002)). Real-time PCR is based on the detection and quantitation of a fluorescent reporter. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. There are two general methods for the quantitative detection of the amplicon: (1) use of fluorescent probes; or (2) use of DNA-binding agents (e.g., SYBR-green I or ethidium bromide). For relative gene expression comparisons, it is necessary to use an endogenous control as an internal reference (e.g., the chromosomally encoded 16S rRNA gene), thereby allowing one to normalize for differences in the amount of total DNA added to each real-time PCR reaction. Specific methods for real-time PCR are well documented in the art. See, for example, the Real Time PCR Special Issue (*Methods*, 25(4):383–481 (2001)).

Following a real-time PCR reaction, the recorded fluorescence intensity is used to quantitate the amount of template by use of: 1.) an absolute standard method (wherein a known amount of standard such as in vitro translated RNA (cRNA) is used); 2.) a relative standard method (wherein known amounts of the target nucleic acid are included in the assay design in each run); or 3.) a comparative $C_T$ method ($\Delta\Delta C_T$) for relative quantitation of gene expression (wherein the relative amount of the target sequence is compared to any of the reference values chosen and the result is given as relative to the reference value).

The comparative $C_T$ method requires one to first determine the difference ($\Delta C_T$) between the $C_T$ values of the target and the normalizer, wherein: $\Delta C_T = C_T(\text{target}) - C_T(\text{normalizer})$. This value is calculated for each sample to be quantitated and one sample must be selected as the reference against which each comparison is made. The comparative $\Delta\Delta C_T$ calculation involves finding the difference between each sample's $\Delta C_T$ and the baseline's $\Delta C_T$, and then transforming these values into absolute values according to the formula $2^{-\Delta\Delta C_T}$.

It is thus an aspect of the invention to provide a method for the generation and isolation of plasmid replication control region conveying altered plasmid copy number, comprising:
a) providing a plasmid comprising a replication control region derived from pBBR1;
b) subjecting the plasmid of (a) to a mutagenic procedure wherein mutations are introduced into the replication control region of the plasmid;
c) Transforming the mutant plasmids into a suitable host cell;
d) culturing the said host cell of (c) and determining plasmid copy number;
e) selecting at least one plasmid of (c) which has altered plasmid copy number relative to the plasmid of (a); and
f) isolating mutant replication control regions from the plasmids of (d).

It is envisioned that plasmid copy number could be determined by various means, such as e.g., by use of a reporter construct to indirectly quantitate plasmid copy number based on reporter gene expression, estimation of DNA concentration change on agarose gels, real-time PCR, and Northern blot analysis.

Plasmids Having Increased Plasmid Copy Number

Replication control regions of the present invention were mutagenized, introduced into host cells and screened for plasmids which replicate with increased copy number in the host (according to expression levels of a reporter construct). The desired plasmids were then re-isolated and the replication control region of each was sequenced. When each mutant plasmid replication control region (SEQ ID NOs:6, 8, 10, 12, 13, 15, 17, 18, 20, and 21) was compared with the wild-type pBHR1 replication control region (nucleotides 2478–3765 of SEQ ID NO:1), the following mutations were observed:
a) a mutation of G to A at nucleotide 2490;
b) a mutation of C to T at nucleotide 2496;
c) a mutation of T to C at nucleotide 2579;
d) a mutation by deletion of C at nucleotide 2633;
e) a mutation by deletion of C at nucleotide 2634;
f) a mutation of T to C at nucleotide 2663;
g) a mutation of A to G at nucleotide 2771;
h) a mutation of T to C at nucleotide 2805;
i) a mutation of C to A at nucleotide 2838;
j) a mutation of T to C at nucleotide 2914;
k) a mutation of T to C at nucleotide 2935;
l) a mutation of C to T at nucleotide 3003;
m) a mutation for substitution of G to A at nucleotide 3165;
n) a mutation of T to G at nucleotide 3262;
o) a mutation of C to T at nucleotide 3269;
p) a mutation of T to C at nucleotide 3344;
q) a mutation of C to T at nucleotide 3347;
r) a mutation for substitution of G to A at nucleotide 3456;
s) a mutation for substitution of T to C at nucleotide 3468;
t) a mutation for substitution of A to G at nucleotide 3570;
u) a mutation of T to C at nucleotide 3604;
v) a mutation of A to C at nucleotide 3641;
w) a mutation of A to G at nucleotide 3729;
x) a mutation of T to A at nucleotide 3739; and
y) a mutation of T to C at nucleotide 3747.

These mutations had the effect of conveying increased plasmid copy number to the plasmid on which the mutant replication control region resided. One other mutation (i.e., a mutation by insertion of C at nucleotide 3030) was present in each mutant plasmid replication control region with respect to the wild-type pBHR1 replication control region; however, this particular mutation did not appear to affect plasmid copy number.

A representative mutant rep gene (SEQ ID NO:3) which will convey increased plasmid copy number to the plasmid on which the mutant replication gene resides, may optionally contain at least one point mutation independently selected from the group consisting of:
a) a mutation for substitution of G to A at nucleotide 117 (corresponding to position 3165 of SEQ ID NO:1);
b) a mutation of T to G at nucleotide 214 (corresponding to position 3262 of SEQ ID NO:1);
c) a mutation of C to T at nucleotide 221 (corresponding to position 3269 of SEQ ID NO:1);
d) a mutation of T to C at nucleotide 296 (corresponding to position 3344 of SEQ ID NO:1);
e) a mutation of C to T at nucleotide 299 (corresponding to position 3347 of SEQ ID NO:1);
f) a mutation for substitution of G to A at nucleotide 408 (corresponding to position 3456 of SEQ ID NO:1);
g) a mutation for substitution of T to C at nucleotide 420 (corresponding to position 3468 of SEQ ID NO:1);
h) a mutation for substitution of A to G at nucleotide 522 (corresponding to position 3570 of SEQ ID NO:1);
i) a mutation of T to C at nucleotide 556 (corresponding to position 3604 of SEQ ID NO:1); and
j) and a mutation of A to C at nucleotide 593 (corresponding to position 3641 of SEQ ID NO:1).

It is contemplated that other sequences having the same or other mutations in this particular replication control region will give rise to a phenotype of altered plasmid copy number. It will be expected, for example, that sequences having a high degree of homology to the present sequences and having the appropriate mutations will also convey increased plasmid copy number. Thus it is an aspect of the invention to provide a mutant replication control region which: 1.) conveys altered plasmid copy number to a plasmid; and 2.) hybridizes to the mutant nucleotide sequence of the invention under the following conditions 0.1×SSC, 0.1% SDS, 65° C. and washed with 2×SSC, 0.1% SDS followed by 0.1×SSC, 0.1% SDS, to provide a mutant replication control region that conveys altered plasmid copy number to a plasmid and is at least 90% identical to the nucleotide sequence of the mutant replication region of the invention. Another embodiment of the present invention is to provide a mutant replication control region that conveys altered plasmid copy number to a plasmid and is at least 95% identical to the nucleotide sequence of the mutant replication region of the invention. An additional embodiment is to provide a mutant replication control region that conveys altered plasmid copy number to a plasmid and is at least 98% identical to the nucleotide sequence of the mutant replication region of the invention.

Recombinant Expression in Microorganisms

The mutant plasmids described herein may be useful for the production of various genes and gene products in heterologous host cells, particularly in the cells of Gram-negative microbial hosts.

Methods for construction of an expression vector based upon the mutant replication control regions of the present invention and containing regulatory sequences that direct high-level expression of foreign proteins are well known to those skilled in the art. Typically the vector or cassette contains sequences directing transcription and translation of the desired gene(s) and a selectable marker. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of ORFs in the desired host cell are numerous and familiar to those skilled in the art. Virtually any promoter capable of driving these genes is suitable for the present invention including, but not limited to: CYC1, HIS3, GAL1, GAL10, ADH1, PGK, PHO5, GAPDH, ADC1, TRP1, URA3, LEU2, ENO, TPI (e.g., useful for expression in *Saccharomyces*); AOX1 (e.g., useful for expression in *Pichia*); and lac, ara, tet, trp, $IP_L$, $IP_R$, T7, tac, and trc (e.g., useful for expression in *Escherichia coli*) as well as the amy, apr, npr promoters and various phage promoters useful for expression in, e.g., *Bacillus*. Additionally, the deoxy-xylulose phosphate synthase or methanol dehydrogenase operon promoter (Springer et al., *FEMS Microbiol Lett*, 160:119–124 (1998)), the promoter for polyhydroxyalkanoic acid synthesis (Foellner et al., *Appl. Microbiol. Biotechnol.*, 40:284–291 (1993)), promoters identified from native plasmids in methylotrophs (EP 296484), *Plac* (Toyama et al., *Microbiology*, 143:595–602 (1997); EP 62971), *Ptrc* (Brosius et al., *Gene*, 27:161–172 (1984)), promoters isolated from the nrtA, glnB, moxF, glyoxII, htpG, and hps genes useful for expression in *Methylomonas* (U.S. Ser. No. 10/689200; hereby incorporated by reference), and promoters associated with antibiotic resistance [e.g., kanamycin (Springer et al., supra; Ueda et al. *Appl. Environ. Microbiol.* 57:924–926 (1991)), tetracycline (U.S. Pat. No. 4,824,786), and the chloramphenicol resistance gene promoter) are suitable for expression in C1 metabolizers.

It is necessary to include an artificial ribosomal binding site ("RBS") upstream of a gene to be expressed when the RBS is not provided by the vector. This is frequently required for the second, third, etc. gene(s) of an operon to be expressed, when a single promoter is driving the expression of a first, second, third, etc. group of genes. Methodology to determine the preferred sequence of a RBS in a particular host organism will be familiar to one of skill in the art, as are means for creation of this synthetic site.

Termination control regions may also be derived from various genes native to the preferred hosts. Optionally, a termination site may be unnecessary; however, it is most preferred if included.

For the plasmid to be a useful tool, it generally will contain a selectable marker. Selectable markers are common and well known in the art and typically are those genes that convey antibiotic resistance to the host cell. Suitable selectable markers for use in the present invention include, but are not limited to: genes encoding ampicillin (Amp) resistance, kanamycin (Kan) resistance, tetracycline resistance, chloramphenicol resistance, and spectinomycin resistance. Also suitable as genetic markers are those genes encoding metal resistance, substrate-utilization, and genes encoding fluorescent and bioluminescent proteins (e.g., green fluorescent proteins, Lux genes), as well as lacZ, gfp, cat, galK, inaZ, luc, luxAB, bgaB, nptII, phoA, uidA and xylE. Other suitable bacterial and yeast markers may be found in Sambrook, J. et al., supra.

One fortuitous aspect of the plasmids of the invention is that the replication control region differs from conventionally known plasmids (e.g., plasmids belonging to the incompatibility groups C, N, P, Q and W), and it is not incompatible with these plasmids. Thus, these plasmids can be used in microbes together with more common plasmids belonging to the incompatibility groups C, N, P, Q and W. It is expected that the plasmids of the present invention will function in all Gram-negative bacteria and will be particularly useful in the following genera: *Acetobacter, Acinetobacter, Aeromonas, Agrobacterium, Alcaligenes, Anabaena, Azorizobium, Bartonella, Bordetellá, Brucella, Burkholderia, Campylobacter, Caulobacter, Chromatium, Comamonas, Cytophaga, Deinococcus, Erwinia, Erythrobacter, Escherichia, Flavobacterium, Hyphomicrobium, Klebsiella, Methanobacterium, Methylbacterium, Methylobacillus, Methylobacter, Methylobacterium, Methylococcus, Methylocystis, Methylomicrobium, Methylomonas, Methylophilus, Methylosinus, Myxococcus, Pantoea, Paracoccus, Pseudomonas, Rhizobium, Rhodobacter, Salmonella, Shigella, Sphingomonas, Vibrio, Arthrobacter, Bacillus, Methanomonas, Nocardia, Rhodopseudomonas, Xanthobacter, Bradyrhizobium,* and *Brevundimonas*.

C1 Metabolizing Bacteria and *Methylomonas* sp. 16a as Microbial Hosts

There are a number of microorganisms that utilize single carbon substrates as their sole energy source. Such microorganisms are referred to herein as "C1 metabolizers". These organisms are characterized by the ability to use carbon substrates lacking carbon to carbon bonds as a sole source of energy and biomass. These carbon substrates include, but are not limited to: methane, methanol, formate, formaldehyde, formic acid, methylated amines (e.g., mono-, di- and trimethyl amine), methylated thiols, carbon dioxide, and various other reduced carbon compounds which lack any carbon-carbon bonds.

All C1 metabolizing microorganisms are generally classified as methylotrophs. Methylotrophs may be defined as any organism capable of oxidizing organic compounds that do not contain carbon-carbon bonds. However, facultative methylotrophs, obligate methylotrophs, and obligate methanotrophs are all various subsets of methylotrophs. Specifically:

Facultative methylotrophs have the ability to oxidize organic compounds which do not contain carbon-carbon bonds, but may also use other carbon substrates such as sugars and complex carbohydrates for energy and biomass. Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1 Compounds., [Int. Symp.], 7th* (1993), pp 285–302. Murrell, J. Collin and Don P. Kelly, Eds. Intercept: Andover, UK; Madigan et al., *Brock Biology of Microorganisms, 8th* ed., Prentice Hall: UpperSaddle River, N.J. (1997)).

Obligate methylotrophs are those organisms that are limited to the use of organic compounds that do not contain carbon-carbon bonds for the generation of energy.

Obligate methanotrophs are those obligate methylotrophs that have the distinct ability to oxidize methane.

Additionally, the ability to utilize single carbon substrates is not limited to bacteria but extends also to yeasts and fungi. A number of yeast genera are able to use single carbon substrates as energy sources in addition to more complex materials (i.e., the methylotrophic yeasts).

Although a large number of these methylotrophic organisms are known, few of these microbes have been successfully harnessed in industrial processes for the synthesis of materials. Although single carbon substrates are cost-effective energy sources, difficulty in genetic manipulation of these microorganisms as well as a dearth of information about their genetic machinery has limited their use primarily to the synthesis of native products.

Despite these limitations, facultative methylotrophic bacteria suitable in the present invention include, but are not limited to: *Methylophilus*, *Methylobacillus*, *Methylobacterium*, *Hyphomicrobium*, *Xanthobacter*, *Bacillus*, *Paracoccus*, *Nocardia*, *Arthrobacter*, *Rhodopseudomonas*, and *Pseudomonas*. Exemplary methanotrophs include, but are not limited to, the genera *Methylomonas*, *Methylobacter*, *Methylococcus*, *Methylosinus*, *Methylocystis*, *Methylomicrobium*, and *Methanomonas*.

Of particular interest in the present invention are host organisms that are high growth obligate methanotrophs having an energetically favorable carbon flux pathway. In one embodiment, the host organism is *Methylomonas* 16a (ATCC PTA 2402) (U.S. Pat. No. 6,689,601; hereby incorporated by reference). It has been demonstrated that various heterologous genes can be expressed in this organism (WO 02/18617; corresponding to U.S. Pat. No. 09/941947, hereby incorporated by reference).

Industrial Production of Plasmid Expression Products in a Recombinant Microbial Host Where commercial production of a specific protein(s) expressed from a plasmid of the invention herein is desired, a variety of culture methodologies may be applied. For example, large-scale production of a specific gene product expressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur (while adding nothing to the system). Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase, where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art; examples may be found in Brock (supra) and Deshpande (supra).

Commercial production of a specific product expressed on a plasmid may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art of industrial microbiology and a variety of methods are detailed by Brock, supra.

Description of the Embodiments

As specific examples of the plasmids of the present invention, the following plasmids having increased plasmid copy number can be mentioned (each further described in the Examples below): pDCQ318M1, pDCQ318M2, pDCQ318M3, pDCQ318M4, pDCQ318M5, pDCQ318M7, pDCQ318M8, pDCQ318M14, pDCQ318M32, and pDCQ318M35. These plasmids encompass one or more of the following mutations relative to the wild-type replication control region of pBHR1, wherein the replication control region is defined therein as nucleotides 2478–3765 of SEQ ID NO:1 of the wild-type pBHR1 vector (GenBank® Accession No. Y14439):

a) a mutation of G to A at nucleotide 2490;
b) a mutation of C to T at nucleotide 2496;
c) a mutation of T to C at nucleotide 2579;
d) a mutation by deletion of C at nucleotide 2633;
e) a mutation by deletion of C at nucleotide 2634;
f) a mutation of T to C at nucleotide 2663;
g) a mutation of A to G at nucleotide 2771;
h) a mutation of T to C at nucleotide 2805;
i) a mutation of C to A at nucleotide 2838;
j) a mutation of T to C at nucleotide 2914;
k) a mutation of T to C at nucleotide 2935;
l) a mutation of C to T at nucleotide 3003;
m) a mutation for substitution of G to A at nucleotide 3165;
n) a mutation of T to G at nucleotide 3262;
o) a mutation of C to T at nucleotide 3269;
p) a mutation of T to C at nucleotide 3344;
q) a mutation of C to T at nucleotide 3347;
r) a mutation for substitution of G to A at nucleotide 3456;
s) a mutation for substitution of T to C at nucleotide 3468;
t) a mutation for substitution of A to G at nucleotide 3570;
u) a mutation of T to C at nucleotide 3604;
v) a mutation of A to C at nucleotide 3641;

w) a mutation of A to G at nucleotide 3729;
x) a mutation of T to A at nucleotide 3739; and
y) a mutation of T to C at nucleotide 3747.

For reference, the rep gene is encoded between nucleotides 3049–3711 of SEQ ID NO:1.

Each of the plasmids described herein was isolated following error-prone PCR reactions to create mutations within the replication control region. These mutant sequences were then used to replace the native replication control region of a reporter plasmid based on pBHR1. This reporter plasmid carried the crtEYIB genes, which encode for the enzymes responsible for the synthesis of the yellow-pigmented carotenoid β-carotene. Use of this reporter plasmid permitted easy visual screening of the amount of β-carotene produced by each transformant *E. coli* host, as a means to indirectly quantify changes in plasmid copy number. Following the identification of a number of clones over-producing β-carotene, subsequent analysis:

1. Confirmed that the replication control region within each plasmid possessed at least one or more mutations with respect to the wild-type replication control region of pBHR1 that had not been subjected to error-prone PCR; and
2. Confirmed, by real-time PCR, that the plasmid copy number of these mutants had increased relative to the plasmid copy number of control plasmids carrying the wild-type replication control region of pBHR1 that had not been subjected to error-prone PCR.

The plasmids identified herein will be useful as a means to rapidly optimize levels of gene expression of heterologous plasmid-borne genes within a particular host cell since overall expression levels fluctuate according to plasmid copy number.

In one embodiment, the plasmid copy number of the present plasmids comprised of a mutant replication control region is altered in comparison to the plasmid copy number associated with a plasmid comprised of the wild type replication control region of pBBR1 when assayed under identical conditions (i.e. same host under identical growth conditions). In another embodiment, the plasmid copy number of the present plasmids comprised of a mutant replication control region is increased in comparison to the plasmid copy number associated with a plasmid comprised of the wild type replication control region of pBBR1. In a further embodiment, the plasmid copy number of the present plasmids comprised of a mutant replication control region is increased at least about 2-fold in comparison to the plasmid copy number associated with a plasmid comprised of the wild type replication control region of pBBR1. In yet a further embodiment, the plasmid copy number of the present plasmids comprised of a mutant replication control region is increased at least about 5-fold in comparison to the plasmid copy number associated with a plasmid comprised of the wild type replication control region of pBBR1.

The present work described herein makes use of the crtEYIB carotenoid cluster for production of β-carotene; merely as a convenient reporter molecule for indirect visual determination of relative plasmid copy number. There is a general practical utility for microbial production of carotenoid compounds since these compounds are very difficult to make chemically (Nelis and Leenheer, *Appl. Bacteriol.*, 70:181–191 (1991)). Industrially only a few carotenoids are used for food colors, animal feeds, pharmaceuticals, and cosmetics, despite the existence of more than 600 different carotenoids identified in nature. Most carotenoids have strong color and can be viewed as natural pigments or colorants. Furthermore, many carotenoids have potent antioxidant properties and thus inclusion of these compounds in the diet is thought to be healthful.

A variety of methods for carotenoid production based on microbial platforms have recently been described in the art [e.g., *E. coli* and *Candia utilis* for production of lycopene (Farmer W. R. and J. C. Liao., *Biotechnol. Prog.*, 17: 57–61 (2001); Wang C. et al., *Biotechnol Prog.*, 16: 922–926 (2000); Misawa, N. and H. Shimada., *J. Biotechnol.*, 59: 169–181 (1998); Shimada, H. et al., *Appl. Environm. Microbiol.*, 64:2676–2680 (1998)); *E. coli*, *Candia utilis*, and *Pfaffia rhodozyma* for production of β-carotene (Albrecht, M. et al., *Biotechnol. Lett.*, 21: 791–795 (1999); Miura, Y. et al., *Appl. Environm. Microbiol.*, 64:1226–1229 (1998); and U.S. Pat. No. 5,691,190); *E. coli* and *Candia utilis* for production of zeaxanthin (Albrecht, M. et al., supra; Miura, Y. et al., supra); *E. coli* and *Pfaffia rhodozyma* for production of astaxanthin (U.S. Pat. No. 5,466,599; U.S. Pat. No. 6,015,684; U.S. Pat. No. 5,182,208; and U.S. Pat. No. 5,972,642); see also: U.S. Pat. No. 5,656,472, U.S. Pat. No. 5,545,816, U.S. Pat. No. 5,530,189, U.S. Pat. No. 5,530,188, U.S. Pat. No. 5,429,939, and U.S. Pat. No. 6,124,113)]. However, these methods of producing carotenoids suffer from low yields and reliance on relatively expensive feedstocks. Thus, it would be desirable to identify a method that produces higher yields of carotenoids in a microbial host from an inexpensive feedstock.

Recently, Odom et al. have demonstrated that the C1 metabolizing bacteria *Methylomonas* sp. 16a can be engineered for production of various $C_{40}$ carotenoids (WO 02/18617), by the introduction of one or more of the lower $C_{40}$ carotenoid biosynthetic pathway genes (i.e., crtM, crtN, crtN2, crtE, crtX, crtY, crtI, crtB, crtZ, crtW, crtO, crtA, crtC, crtD, crtF, and crtU). This organism is particularly well suited for industrial scale production of carotenoids, since:

1. It is capable of efficiently using either methanol or methane as a carbon substrate;
2. It is metabolically versatile in that it contains multiple pathways for the incorporation of carbon from formaldehyde into 3-carbon units;
3. It is capable of genetic exchange with donor species such as *Escherichia coli* via bacterial conjugation; and
4. The organism contains an inherent isoprenoid pathway that enables the production of $C_{30}$ pigments.

Despite the previous demonstration of β-carotene production in this unique microbial host, further advancement towards creation of a recombinant host suitable for high-level production of a specific carotenoid product will require significant metabolic engineering to the native host machinery and biosynthetic pathways. For example, it will be necessary to substantially increase the titer of β-carotene production. The present invention will be particularly useful for efforts targeted toward the genetic engineering of C1 metabolizing bacteria such as *Methylomonas* sp. 16a, as a means to rapidly investigate the advantages of increased gene expression in a particular host by increasing plasmid copy number.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

GENERAL METHODS

Standard recombinant DNA and molecular cloning techniques used in the Examples are well known in the art and are described by Sambrook et al. (supra); by Silhavy et al. (supra); and Ausubel et al., (supra).

Materials and methods suitable for the maintenance and growth of bacterial cultures are well known in the art. Techniques suitable for use in the following examples may be found as set out in: *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Brock (supra).

Sequence was generated on an ABI Automatic sequencer using dye terminator technology (U.S. Pat. No. 5,366,860; EP 272,007) using a combination of vector and insert-specific primers. Sequence editing and assembly was performed in Sequencher program (Gene Codes Corp., Ann Arbor, Mich.). Alignment of mutant sequences with the wild type sequence was performed using AlignX program in the VectorNTI Suite 6.0 (InforMax, Inc., Bethesda, Md.).

Restriction enzyme digestions, phosphorylations, ligations, and transformations were done as described in Sambrook, J. et al., supra. Restriction enzymes were obtained from New England Biolabs (Boston, Mass.), GIBCO/BRL (Gaithersburg, Md.), or Promega (Madison, Wis.). Taq polymerase was obtained from Perkin Elmer (Branchburg, N.J.). Growth media was obtained from GIBCO/BRL (Gaithersburg, Md.).

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s), and "kB" means kilobase(s).

Example 1

Construction of pBHR1 Based Reporter Plasmids

This example describes cloning of a carotenoid synthesis gene cluster for use as a reporter construct and its insertion into the pBHR1 vector backbone. Two plasmids were constructed for this study: pDCQ301 and pDCQ318. pDCQ301 contains a crtEYIB gene cluster cloned into the EcoRI site of the pBHR1 vector. pDCQ318 contains a deletion of the downstream region of the rep gene from pDCQ301.

Amplification of the *Pantoea stewartii* crtEYIB Gene Cluster

The carotenoid synthesis genes crtEYIB encode enzymes for synthesis of β-carotene, which was used as a reporter molecule for mutant screening in this application. *Pantoea stewartii* ATCC #8199 (WO 03/016503) contains the natural gene cluster crtEXYIBZ. The genes required for β-carotene synthesis (i.e., crtE and crtYIB) were joined together by PCR. Specifically, the crtE gene and crtYIB genes were each amplified using chromosomal DNA as template and the following primers:

TABLE 2

Primers Used for Creation of the crtEYIB
Reporter Construct

| Gene(s) | Forward Primer | Reverse Primer |
|---|---|---|
| crtE | pBHRcrt_1F:<br>5'-<u>GAATTC</u>GCCCTTGACG<br>GTCT-3'<br>(SEQ ID NO:22) | pBHRcrt_1R:<br>5'-CGGTTGCATAATCCTGCC<br>CACT<u>CAATTG</u>TTAACTGACGGC<br>AGCGAGTTTT-3'<br>(SEQ ID NO:23) |
| crtYIB | pBHRcrt_2F:<br>5'-AAAACTCGCTGCCGTC<br>AGTTAA<u>CAATTG</u>AGTGGG<br>CAGGATTATGCAACCG-3'<br>(SEQ ID NO:24) | pBHRcrt_2R:<br>5'-<u>GGTACC</u>TAGATCGGGC<br>GCTGCCAGA-3'<br>(SEQ ID NO:25) |

*Note: Underlined portions within each primer correspond to restriction sites for EcoR I, Mfe I or Kpn I. The Kpn I site was added to facilitate the construction of pDCQ318 (to be described below).

The PCR reactions were performed with Pfu DNA polymerase in buffer supplied by the manufacturer containing dNTPs (200 μM of each). Parameters for the thermocycling reactions were: 92° C. (5 min), followed by 30 cycles of: 95° C. (30 sec), 55° C. (30 sec), and 72° C. (5 min). The reaction concluded with 1 cycle at 72° C. for 10 min.

The two PCR products were gel purified and joined together by a subsequent PCR reaction using the primers pBHRcrt_1F and pBHRcrt_2R (SEQ ID NOs: 22 and 25). Parameters for the thermocycling reaction were: 95° C. (5 min), followed by 20 cycles of: 95° C. (30 sec), 55° C. (1 min) and 72° C. (8 min). A final elongation step at 72° C. for 10 min completed the reaction. The final 4511 bp PCR product was cloned into the pTrcHis2-Topo vector (Invitrogen, Carlsbad, Calif.) in the forward orientation, resulting in plasmid pDCQ300.

Construction of Reporter Plasmids pDCQ301 and pDCQ318

The ~4.5 kb EcoRI fragment of pDCQ300 containing the crtEYIB gene cluster was ligated into the unique EcoRI site of vector pBHR1 (MoBiTec GmbH, Goettingen, Germany), to create construct pDCQ301. This reporter plasmid had the crtEYIB genes under the control of the chloramphenicol resistant gene promoter of pBHR1 (see FIG. 1); a 2152 bp sequence of pDCQ301 comprising the rep gene is provided as SEQ ID NO:35.

A second reporter plasmid designated as pDCQ318 was constructed from pDCQ301. pDCQ318 was created for use in subsequent error-prone PCR mutagenesis reactions (see Example 2). This derivative had a shortened 3' flanking region of the rep gene relative to pDCQ301. As shown in FIG. 1, approximately 860 bp were removed from the 3' flanking region of the rep gene.

Specifically, the rep gene and its 5' and 3' flanking regions were PCR amplified using primers 301rep_F (SEQ ID NO:26) and 301rep_R (5'-CGG <u>GGTACC</u>GAATTCTACAGCCGATAGTCTGGAACAGC-3'; SEQ ID NO:27) and pDCQ301 as template. The underlined portion of primer 301rep_R corresponds to an engineered KpnI site.

Following the PCR reaction, the 1388 bp PCR product was digested with XhoI and KpnI, and ligated into XhoI and KpnI digested pDCQ301. This resulted in the creation of pDCQ318. Thus, the original rep gene present in parental plasmids pBHR1 and pDCQ301 was replaced with one having a shorter 3' flanking region in pDCQ318.

Example 2

Isolation of Mutant Derivatives of Plasmid PDCQ318 that Show Increased Carotenoid Production This example describes how error-prone PCR was used to introduce mutations into the replication control region of plasmid pDCQ318, resulting in increased □-carotene production. Specifically, the replication control region was first amplified by error-prone PCR from pDCQ318. The resulting PCR product was ligated into a restriction fragment derived from pDCQ318, such that the original replication control region of pDCQ318 was replaced with the products of the error-prone PCR reaction. Ten mutant plasmids were identified that resulted in increased carotenoid production in E. coli.

Construction of pDCQ318 Mutant Plasmid Library by Error-Prone PCR

Error-prone PCR was performed to amplify a 1461 bp fragment from pDCQ318 that contained the native rep gene (corresponding to nucleotides 3049–3711 of pBHR1, provided in SEQ ID NO:1). Each PCR reaction was performed with AmpliTaq DNA polymerase (Applied Biosystems, Foster City, Calif.) in buffer supplied by the manufacturer (GeneAmp® 10×PCR Buffer II) containing $MgCl_2$ (250 µM), dNTPs (200 µM of each), primers (pBHR1rep_F [SEQ ID NO:28] and 301rep_R2 [SEQ ID NO:29]), and pDCQ318 DNA (10 ng) as template. In addition, each reaction contained from 50 to 250 µM $MnCl_2$. The reactions were incubated in a Perkin Elmer GeneAMP 9600 initially for 5 min at 95° C. and then for 35 cycles at 92° C. for 1 min, 55° C. for 1 min, and 72° C. for 1 min. After the last cycle, the samples were incubated at 72° C. for an additional 10 min.

The amplified DNA was purified using a DNA Clean & Concentrator™ Kit according to the manufacturer's instructions (Zymo Research, Orange, Calif.). The purified PCR products from reactions that contained 50, 75, 100, 125, 150 and 200 µM $MnCl_2$ were mixed and digested with restriction endonucleases KpnI and XhoI. A 1,300 bp KpnI/XhoI restriction fragment was purified by electrophoresis in 1% agarose in TBE buffer, followed by excision of the appropriate bands and extraction from the excised agarose using a Zymoclean Gel DNA Recovery Kit according to the manufacturer's instructions (Zymo Research).

The purified KpnI/XhoI digested error-prone PCR product was ligated to KpnI/XhoI digested pDCQ318 to replace the wild-type replication control region using T4 DNA ligase (Invitrogen Corporation, Carlsbad, Calif.) according to standard methods at 16° C. for 16 h. The ligated DNA was electroporated into electrocompetent E. coli XL1-blue MRF' cells (Stratagene, La Jolla, Calif.) using a BioRad Gene Pulser II (BioRad Laboratories, Hercules, Calif.) according to standard methods (voltage 1.8 kV, capacitance 25 µF, and 200 ohms). The transformed cells were spread on LB agar containing 50 µg/mL kanamycin and incubated for 3–4 days at 30° C.

Identification of Mutant Plasmids that Showed Increased β-carotene Production

Transformants on LB agar plates were monitored for up to 4 days at 30° C. Three dozen clones that showed intense yellow color were streaked out for β-carotene quantitation. Each mutant was inoculated into two wells of a 24 well culture block (Qiagen Inc, Valencia, Calif.). Each well contained 2.5 mL LB medium with 50 µg/mL kanamycin. Cells were grown at 30° C. with shaking at 220 rpm for 3 days. XL1-blue MRF' cells containing pDCQ301 and XL1-blue MRF' cells containing pDCQ318 were used as controls.

After 3 days of growth, cell densities of each E. coli control and mutant culture were recorded by measuring $OD_{600}$. Cells were spun down for 15 min at 4000 g. Carotenoids were extracted from cell pellets in 0.5 mL tetrahydrofuran for 10 min at room temperature. The relative amount of β-carotene produced was recorded by measuring $OD_{455}$ and normalized by cell density. The $OD_{455}/OD_{600}$ value for each mutant was compared with that of the controls. The relative amount of β-carotene produced in ten mutants (i.e., pDCQ318M1, pDCQ318M2, pDCQ318M3, pDCQ318M4, pDCQ318M5, pDCQ318M7, pDCQ318M8, pDCQ318M14, pDCQ318M32, and pDCQ318M35) are shown in FIG. 2. These ten mutants showed the highest increase in β-carotene production among the three-dozen mutants tested, with production ranging from about 2.19 to 2.72 units. Error bars correspond to 1 standard deviation.

Example 3

Sequence of the Replication Control Region in plasmid DDCQ318 and its Mutant Derivatives This example describes the sequences of the mutant replication control regions in ten plasmid derivatives of pDCQ318 that over-produced β-carotene. Sequence analysis indicated that the error-prone PCR mutagenesis reactions had resulted in at least one or more mutations in each mutant plasmid, with respect to the rep gene and its flanking sequences in pDCQ318.

Sequencing of Mutant Replication Control Regions

The ten mutants that showed the highest increase in β-carotene production (i.e., pDCQ318M1, pDCQ318M2, pDCQ318M3, pDCQ318M4, pDCQ318M5, pDCQ318M7, pDCQ318M8, pDCQ318M14, pDCQ318M32, and pDCQ318M35; see FIG. 2) were selected for further characterization. Each mutant was inoculated into 10 mL LB medium in a 150-mL flask with 50 µg/mL kanamycin and cultured at 220 rpm at 37° C. for 17 h. Plasmid DNA was extracted from 1.5 mL cells using a QIAprep® Spin Miniprep Kit (Qiagen Inc, Valencia, Calif.).

The replication control region of each plasmid was sequenced using 301rep_F primer (SEQ ID NO:26) and 301rep_R2 primer (SEQ ID NO:29).

Sequence Analysis

The portion of each assembled sequence between the KpnI and XhoI restriction sites was aligned with the corresponding pBHR1 sequence (nucleotides 2478–3765 of SEQ ID NO:1) using AlignX, a component of the VectorNTI Suite 6.0 (InforMax, Inc., Bethesda, Md.). The rep gene corresponds to nucleotides 3049 to 3711 of SEQ ID NO:1.

All mutations (both nucleotide and corresponding amino acid) are summarized below in Table 3; additionally, the differences between pDCQ318 and the mutant plasmids are summarized in FIG. 3 (although the insertion of cytosine at nucleotide position 3030 in pDCQ318 and each of the mutant derivatives is not shown in FIG. 3). In both the Table 3 and the FIG. 3, mutations are numbered using the corresponding base pair positions in pBHR1.

TABLE 3

Error-Prone PCR Mutations Generated within the Replication Control Region, Relative to pBHR1(Wild type)

| Strain | Mutation (Nucleotide) | Mutation (Amino Acid) |
|---|---|---|
| pBHR1 (nucleotides 2478–3765 of SEQ ID NO: 1) | None | none |
| pDCQ318 (parent) (SEQ ID NO: 4) | C insertion at 3030 | Upstream of coding region |
| pDCQ318M1 (SEQ ID NO: 6) | C insertion at 3030 | Upstream of coding region |
| | T to G at 3262 | Leu72 to Val |
| | T to C at 3344 | Val99 to Ala |
| pDCQ318M2 (SEQ ID NO: 8) | C insertion at 3030 | Upstream of coding region |
| | C to T at 3347 | Ser100 to Leu |
| pDCQ318M3 (SEQ ID NO: 10) | C to T at nucleotide 2496 | Upstream of coding region |
| | deletion of C at nucleotide 2634 | Upstream of coding region |
| | T to C at nucleotide 2805 | Upstream of coding region |
| | C insertion at 3030 | Upstream of coding region |
| | C to T at nucleotide 3269 | Thr74 to Met |
| | T to C at nucleotide 3604 | Trp186 to Arg |
| pDCQ318M4 (SEQ ID NO: 12) | T to C at nucleotide 2663 | Upstream of coding region |
| | A to G at nucleotide 2771 | Upstream of coding region |
| | C to T at nucleotide 3003 | Upstream of coding region |
| | C insertion at 3030 | Upstream of coding region |
| pDCQ318M5 (SEQ ID NO: 13) | deletion of C at nucleotide 2634 | Upstream of coding region |
| | C insertion at 3030 | Upstream of coding region |
| | G to A at nucleotide 3165 | Silent |
| | C to T at nucleotide 3347 | Ser100 to Leu |
| pDCQ318M7 (SEQ ID NO: 15) | Deletion of C at nucleotide 2633 | Upstream of coding region |
| | Deletion of C at nucleotide 2634 | Upstream of coding region |
| | C insertion at 3030 | Upstream of coding region |
| | C to T at nucleotide 3347 | Ser100 to Leu |
| | A to G at nucleotide 3729 | Downstream of coding region |
| pDCQ318M8 (SEQ ID NO: 17) | C to T at nucleotide 3003 | Upstream of coding region |
| | C insertion at 3030 | Upstream of coding region |
| pDCQ318M14 (SEQ ID NO: 18) | T to C at nucleotide 2914 | Upstream of coding region |
| | T to C at nucleotide 2935 | Upstream of coding region |
| | C insertion at 3030 | Upstream of coding region |
| | C to T at nucleotide 3347 | Ser100 to Leu |
| | A to G at nucleotide 3570 | Silent |
| | A to C at nucleotide 3641 | Asp198 to Ala |
| pDCQ318M32 (SEQ ID NO: 20) | G to A at nucleotide 2490 | Upstream of coding region |
| | T to C at nucleotide 2579 | Upstream of coding region |
| | Deletion of C at nucleotide 2634 | Upstream of coding region |
| | C to A at nucleotide 2838 | Upstream of coding region |
| | C to T at nucleotide 3003 | Upstream of coding region |
| | C insertion at 3030 | Upstream of coding region |
| | G to A at nucleotide 3456 | Silent |
| | T to A at nucleotide 3739 | Downstream of coding region |
| pDCQ318M35 (SEQ ID NO: 21) | C to T at nucleotide 3003 | Upstream of coding region |
| | C insertion at 3030 | Upstream of coding region |
| | G to A at nucleotide 3165 | Silent |
| | T to C at nucleotide 3468 | Silent |
| | T to C at nucleotide 3747 | Downstream of coding region |

*The mutation shown in bold text is the mutation inherited from the parental plasmid, pDCQ318.

pDCQ318 (SEQ ID NO:4) had a-single base pair insertion at nucleotide 3030 when compared to pBHR1. This C3030 insertion, which was 19 bp upstream of the start codon of the rep gene, was generated by PCR during construction of pDCQ318. However, the amount of β-carotene synthesis from pDCQ318 was similar to that from pDCQ301 containing the wild-type rep region (see FIG. 2). Therefore, this mutation was not responsible for the increased carotenoid production observed in pDCQ318M1, pDCQ318M2, pDCQ318M3, pDCQ318M4, pDCQ318M5, pDCQ318M7, pDCQ318M8, pDCQ318M14, pDCQ318M32, and pDCQ318M35. As shown in Table 3, above, all of the pDCQ318 mutants inherited the C3030 insertion mutation from pDCQ318.

Example 4

Determination of Relative Copy Number in Plasmid PDCQ318 and Mutant Derivatives

This example describes the use of real-time PCR to determine the relative plasmid copy number of pDCQ318 and each of the 10 mutant derivatives over-producing β-carotene in *E. coli*. Real-time PCR results indicated that the copy number of the mutant plasmids having mutant replication control regions increased 3–7 fold, as compared to the parental plasmids pDCQ318 and pDCQ301.

Specifically, crude lysate samples of *E. coli* strains containing each of the mutant plasmids (i.e., pDCQ318M1, pDCQ318M2, pDCQ318M3, pDCQ318M4, pDCQ318M5, pDCQ318M7, pDCQ318M8, pDCQ318M14, pDCQ318M32, and pDCQ318M35) were prepared for copy number determination. To prepare crude lysate, each mutant was inoculated into 10 mL LB medium in a 150-mL flask with 50 µg/mL kanamycin and cultured at 220 rpm at 37° C. for 17 h. The cell pellet for each mutant from 1 mL culture was resuspended with 1 mL dH$_2$O. Approximately 0.25 mL of 0.1 mm ZirConia silica beads (Biospec Products, Inc., Bartlesville, Okla.) was added into the cell suspension and the mixture was beaten for 2 min in a BeadBeater (Biospec Products, Inc.) to lyse the cells. The crude lysate was then spun for 10 min at 12,000 g in a micro-centrifuge. Aliquots of 100 µL supernatant from each mutant culture were heated at 99° C. for 10 min to inactivate DNase activity. Seven 1:10 serial dilutions were subsequently made for each crude DNA sample. A sample containing no DNA was also included as a negative control.

PCR primers were designed using the default settings in Primer Express v 2.0 software from Applied Biosystems (Foster City, Calif.). Forward (SEQ ID NO:30) and reverse primers (SEQ ID NO:31) were designed to amplify a 65 bp region at the 3' end of the crtE gene on target plasmid DNA. A 62 bp region of the *E. coli* 16S rRNA gene was also amplified as control DNA using forward (SEQ ID NO:32) and reverse primers (SEQ ID NO:33).

Real time PCR was performed using an Applied Biosystems (ABI) SYBR Green labeling method and monitored on an ABI 7900 Sequence Detection System instrument according to the manufacturer's instructions. Each PCR reaction (20 µL) was set up using the following reagents: 10 µL ABI 2XSYBR Green Master Mix, 0.2 µL each of the forward and reverse primers (100 µM), 8.6 µL water and 1 µL of diluted DNA sample. The thermal cycling conditions used were as follows: 10 min at 95° C. followed by 40 cycles of 95° C., 15 sec and 60° C., 1 min. All reactions were run in triplicate.

Relative quantitation of plasmid copy number was calculated using pDCQ318 as the reference sample. 16S rRNA was used to normalize the quantitation of each sample for differences in the amount of total DNA added to each reaction. The normalized quantity is referred to as the ΔCt. The normalized value for each pDCQ318 mutant was compared to the normalized value of the pDCQ318 reference. This quantity is referred to as the ΔΔCt. The ΔΔCt values were then converted to absolute values by utilizing the formula $2^{-\Delta\Delta Ct}$. These values refer to the fold increase in the copy number of pDCQ318 mutant plasmids, as compared to the pDCQ318 parental plasmid.

The results of the relative quantitation of plasmid copy number for each mutant (i.e., pDCQ318M1, pDCQ318M2, pDCQ318M3, pDCQ318M4, pDCQ318M5, pDCQ318M7, pDCQ318M8, pDCQ318M14, pDCQ318M32, and pDCQ318M35) are shown in FIG. 4, along with 1 standard deviation error bar. The PCR efficiencies of the 16S rRNA gene and the target gene in each sample were close to 100%. This validated the use of the ΔΔCt method for quantitation of relative copy number of plasmid DNA.

The copy number of plasmid pDCQ318 did not change relative to that of pDCQ301. Thus, the insertion of a cytosine base at nucleotide 3030 in pDCQ318 appeared to be a random mutation that did not affect the plasmid copy number. In contrast, the copy numbers of the mutant plasmids increased 3–7 fold compared to that of the parental plasmid pDCQ318 and pDCQ301. The observed increase in copy number was most likely due to the additional mutations shown in Table 3 and FIG. 3, generated by the error-prone PCR mutagenesis reactions. The C3030 insertion inherited from pDCQ318 unlikely contributed to the phenotype of the increased copy number in the mutant plasmids, when they were expressed in *E. coli*.

Example 5

Analysis of pDCQ318 and Mutant Plasmids in *Methylomonas* sp. 16a

The following Example describes the technique that was utilized to introduce pDCQ318 and the representative mutant plasmid (from Example 3) into *Methylomonas* 16a (ATCC PTA 2402) to increase the titer of β-carotene synthesis. The relative copy number of the mutant plasmid in *Methylomonas* 16a was also determined.

Plasmid pDCQ318 and the mutant derivative pDCQ318M2 (comprising a single nucleotide mutation) were transferred into *Methylomonas* 16a by tri-parental conjugal mating. The *E. coli* helper strain containing pRK2013 (ATCC No. 37159) and the *E. coli* XL1 BlueMRF' donor strains containing the plasmids (i.e., pDCQ318 or pDCQ318M2) were each grown overnight in LB medium containing kanamycin (50 µg/mL), washed three times in LB, and resuspended in a volume of LB representing approximately a 60-fold concentration of the original culture volume.

The *Methylomonas* 16a recipient was grown using the general conditions described in WO 02/18617. Briefly, this involves growing *Methylomonas* 16a in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking.

Nitrate Medium for *Methylomonas* 16A

Nitrate liquid medium, also referred to herein as "defined medium" or "BTZ-3" medium is comprised of various salts mixed with Solution 1 as indicated below (Tables 4 and 5) or where specified the nitrate is replaced with 15 mM ammonium chloride. Solution 1 provides the composition for 100-fold concentrated stock solution of trace minerals.

TABLE 4

| Solution 1* | | | |
|---|---|---|---|
| | MW | Conc. (mM) | g per L |
| Nitriloacetic acid | 191.1 | 66.9 | 12.8 |
| CuCl$_2$ × 2H$_2$O | 170.48 | 0.15 | 0.0254 |
| FeCl$_2$ × 4H$_2$O | 198.81 | 1.5 | 0.3 |
| MnCl$_2$ × 4H$_2$O | 197.91 | 0.5 | 0.1 |
| CoCl$_2$ × 6H$_2$O | 237.9 | 1.31 | 0.312 |
| ZnCl$_2$ | 136.29 | 0.73 | 0.1 |
| H$_3$BO$_3$ | 61.83 | 0.16 | 0.01 |
| Na$_2$MoO$_4$ × 2H$_2$O | 241.95 | 0.04 | 0.01 |
| NiCl$_2$ × 6H$_2$O | 237.7 | 0.77 | 0.184 |

*Mix the gram amounts designated above in 900 mL of H$_2$O, adjust to pH = 7, and add H$_2$O to an end volume of 1 L. Keep refrigerated.

TABLE 5

| Nitrate liquid medium (BTZ-3)** | | | |
|---|---|---|---|
| | MW | Conc. (mM) | g per L |
| NaNO$_3$ | 84.99 | 10 | 0.85 |
| KH$_2$PO$_4$ | 136.09 | 3.67 | 0.5 |

TABLE 5-continued

Nitrate liquid medium (BTZ-3)**

| | MW | Conc. (mM) | g per L |
|---|---|---|---|
| Na$_2$SO$_4$ | 142.04 | 3.52 | 0.5 |
| MgCl$_2$ × 6H$_2$O | 203.3 | 0.98 | 0.2 |
| CaCl$_2$ × 2H$_2$O | 147.02 | 0.68 | 0.1 |
| 1 M HEPES (pH 7) | 238.3 | | 50 mL |
| Solution 1 | | | 10 mL |

**Dissolve in 900 mL H$_2$O. Adjust to pH = 7, and add H$_2$O to give 1 L.
For agar plates: Add 15 g of agarose in 1 L of medium, autoclave, let cool down to 50° C., mix, and pour plates.

The standard gas phase for cultivation contains 25% methane in air. Using these conditions, the recipient was cultured for 48 h in BTZ-3 medium, washed three times in BTZ-3, and resuspended in a volume of BTZ-3 representing a 150-fold concentration of the original culture volume.

The donor, helper, and recipient cell pastes were then combined in ratios of 1:1:2, respectively, on the surface of BTZ-3 agar plates containing 0.5% (w/v) yeast extract. Plates were maintained at 30° C. in 25% methane for 16–72 hrs to allow conjugation to occur, after which the cell pastes were collected and resuspended in BTZ-3. Dilutions were plated on BTZ-3 agar containing kanamycin (50 µg/mL) and incubated at 30° C. in 25% methane for up to 1 week. Transconjugants were streaked onto BTZ-3 agar with kanamycin (50 µg/mL) for isolation.

For determination of carotenoid amount, transconjugants were cultured in 20 mL BTZ-3 containing kanamycin (50 µg/mL) and incubated at 30° C. in 25% methane as the sole carbon source for up to 1 week. The cell density was measured by OD600 and β-carotene content was measured by OD455. The relative amount of β-carotene was quantified as OD455/OD600. Cells containing pDCQ318M2 showed approximately 40% increase of β-carotene synthesis compared to that of the control.

Crude extracts were also prepared as described in Example 4 from *Methylomonas* 16a containing various plasmids. The extracts were used for real-time PCR analysis to determine the relative copy number increase of the mutant plasmids in *Methylomonas* 16a. The *Methylomonas* 16S rRNA gene sequence (SEQ ID NO:34) was used for normalization. Results showed that the copy number of the mutant plasmid pDCQ318M2 was more than twice (2.38 fold) than that of the control plasmid in the C1 metabolizing host *Methylomonas* 16a.

What is claimed is:

1. A mutant replication control region having a nucleotide sequence as set forth in nucleotides 2478–3765 of SEQ ID NO:1 and having one point mutation independently selected from the group consisting of:
   a) a mutation of G to A at nucleotide 2490;
   b) a mutation of C to Tat nucleotide 2496;
   c) a mutation of T to C at nucleotide 2579;
   d) a mutation by deletion of C at nucleotide 2633;
   e) a mutation by deletion of C at nucleotide 2634;
   f) a mutation of T to C at nucleotide 2663;
   g) a mutation of A to G at nucleotide 2771;
   h) a mutation of T to C at nucleotide 2805;
   i) a mutation of C to A at nucleotide 2838;
   j) a mutation of T to C at nucleotide 2914;
   k) a mutation of T to C at nucleotide 2935;
   l) a mutation of C to T at nucleotide 3003;
   m) a mutation for substitution of G to A at nucleotide 3165;
   n) a mutation of T to G at nucleotide 3262;
   o) a mutation of C to T at nucleotide 3269;
   p) a mutation of T to C at nucleotide 3344;
   q) a mutation of C to T at nucleotide 3347;
   r) a mutation for substitution of C to A at nucleotide 3456;
   s) a mutation for substitution of T to C at nucleotide 3468;
   t) a mutation for substitution of A to G at nucleotide 3570;
   u) a mutation of T to C at nucleotide 3604;
   v) a mutation of A to C at nucleotide 3641;
   w) a mutation of A to G at nucleotide 3729;
   x) a mutation of T to A at nucleotide 3739; and
   y) a mutation of T to C at nucleotide 3747.

2. A mutant replication gene having the nucleotide sequence as set forth in SEQ ID NO:3 wherein:
   a) nucleotide position 117 is A;
   b) nucleotide position 214 is G;
   c) nucleotide position 221 is T;
   d) nucleotide position 296 is C;
   e) nucleotide position 299 is T;
   f) nucleotide position 408 is A;
   g) nucleotide position 420 is C;
   h) nucleotide position 522 is G;
   i) nucleotide position 556 is C; and
   j) nucleotide position 593 is C.

3. A mutant replication gene as set forth as nucleotides 3049–3711 of SEQ ID NO:1 comprising one point mutation independently selected from the group consisting of:
   a) a mutation for substitution of G to A at nucleotide 117;
   b) a mutation of T to G at nucleotide 214;
   c) a mutation of C to T at nucleotide 221;
   d) a mutation of T to C at nucleotide 296;
   e) a mutation of C to T at nucleotide 299;
   l) a mutation for substitution of G to A at nucleotide 408;
   g) a mutation for substitution of T to C at nucleotide 420;
   h) a mutation for substitution of A to G at nucleotide 522;
   i) a mutation of T to C at nucleotide 556; and
   j) a mutation of A to C at nucleotide 593.

4. A mutant replication control region selected from the group consisting of SEQ ID NOs:6, 8, 10, 12, 13, 14, 15, 17, 18, 20, and 21.

5. A plasmid comprising the mutant replication control region of either of claim 1 or 4.

6. A plasmid comprising the mutant replication gene of any one of claims 2 or 3.

7. The plasmid of claim 5 wherein the plasmid replicates in a Gram-negative bacteria.

8. The plasmid of claim 7 wherein the Gram-negative bacteria is selected from the group consisting of: *Acetobacter, Acinetobacter, Aeromonas, Agrobacterium, Alcaligenes, Anabaena, Azorizobium, Bartonella, Bordetella, Brucella, Burkholderia, Campylobacter, Caulobacter, Chromatium, Comamonas, Cytophaga, Deinococcus, Erwinia, Erythrobacter, Escherichia, Flavobacterium, Hyphomicrobium, Klebsiella, Methanobacterium, Methylbacterium, Methylobacillus, Methylobacter, Methylobacterium, Methylococcus, Methylocystis, Methylomicrobium, Methylomonas, Methylophilus, Methylosinus, Myxococcus, Pantoea, Paracoccus, Pseudomonas, Rhizobium, Rhodobacter, Salmonella, Shigella, Sphingomonas, Vibrio, Arthrobacter Bacillus, Methanomonas, Nocardia, Rhodopseudomonas, Xanthobacter, Bradyrhizobium,* and *Brevundimonas.*

9. A Gram-negative host cell comprising a mutant replication control region according to either of claim 1 or 4.

10. The host cell according to claim 9 selected from the group consisting of: *Acetobacter, Acinetobacter, Aeromonas, Agrobacterium, Alcaligenes, Anabaena, Azorizobium, Bartonella, Bordetella, Brucella, Burkholderia, Campylobacter, Caulobacter, Chromatium, Comamonas, Cytophaga, Deinococcus, Erwinia, Erythrobacter, Escherichia, Flavobacterium, Hyphomicrobium, Klebsiella, Methanobacterium, Methylbacterium, Methylobacillus, Methylobacter, Methylobacterium, Methylococcus, Methylocystis, Methylomicrobium, Methylomonas, Methylophilus, Methylosinus, Myxococcus, Pantoea, Paracoccus, Pseudomonas, Rhizobium, Rhodobacter, Salmonella, Shigella, Sphingomonas, Vibrio, Arthrobacter, Bacillus, Methanomonas, Nocardia, Rhodopseudomonas, Xanthobacter, Bradyrhizobium,* and *Brevundimonas.*

11. A method for regulating gene expression in an organism comprising expressing at least one gene on a plasmid comprising the mutant replication control region of either of claim 1 or 4 in an organism, such that gene expression is altered in the organism relative to expression of the at least one gene on a plasmid comprising the replication control region of pBBR1 in the organism.

12. The method of claim 11, wherein the gene expression is increased.

13. The method of claim 12, wherein:
   a) the at least one gene is selected from the group consisting of: crtM crtN crtN2, crtE crtX crtY, crtI, crtB, crtZ, crtW, crtO, crtA, crtC, crtD, crtF, and crtU; and
   b) the organism is a C1 metabolizing bacteria.

14. The method of claim 13 wherein the C1 metabolizing bacteria is selected from the group consisting of *Methylomonas, Methylobacter, Methylococcus, Methylosinus, Methylocystis, Methylomicrobium,* and *Methanomonas.*

15. A method according to claim 14 wherein the C1 metabolizing host cell is a high growth methanotrophic bacterial strain, known as *Methylomonas* 16a and having the ATCC designation PTA 2402.

* * * * *

SEQUENCE LISTING

```
<160> NUMBER OF SEQ ID NOS: 36

<210> SEQ ID NO 1
<211> LENGTH: 5300
<212> TYPE: DNA
<213> ORGANISM: Escherichia coli (GenBank Accession No. Y14439)
<220> FEATURE:
<221> NAME/KEY: misc_feature
<222> LOCATION: (2478)..(3765)
<223> OTHER INFORMATION: replication control region
<220> FEATURE:
<221> NAME/KEY: CDS
<222> LOCATION: (3049)..(3711)
<223> OTHER INFORMATION: rep gene

<400> SEQUENCE: 1
ctcgggccgt ctcttgggct tgatcggcct tcttgcgcat ctcacgcgct cctgcggcgg        60
cctgtagggc aggctcatac ccctgccgaa ccgcttttgt cagccggtcg gccacggctt       120
ccggcgtctc aacgcgcttt gagattccca gcttttcggc caatccctgc ggtgcatagg       180
cgcgtggctc gaccgcttgc gggctgatgg tgacgtggcc cactggtggc cgctccaggg       240
cctcgtagaa cgcctgaatg cgcgtgtgac gtgccttgct gccctcgatg cccgttgca       300 gcctagatc ggccacagcg gccgcaaacg tggtctggtc gcgggtcatc tgcgctttgt       360
tgccgatgaa ctccttggcc gacagcctgc cgtcctgcgt cagcggcacc acgaacgcgg       420
tcatgtgcgg gctggtttcg tcacggtgga tgctggccgt cacgatgcga tccgccccgt       480
acttgtccgc cagccacttg tgcgccttct cgaagaacgc cgcctgctgt tcttggctgg       540
ccgacttcca ccattccggg ctggccgtca tgacgtactc gaccgccaac acagcgtcct       600
tgcgccgctt ctctggcagc aactcgcgca gtcggcccat cgcttcatcg gtgctgctgg       660
ccgcccagtg ctcgttctct ggcgtcctgc tggcgtcagc gttgggcgtc tcgcgctcgc       720
ggtaggcgtg cttgagactg gccgccacgt tgcccatttt cgccagcttc ttgcatcgca       780
tgatcgcgta tgccgccatg cctgcccctc ccttttggtg tccaaccggc tcgacggggg       840
```

-continued

```
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
ttcgccctgc gcggtcgctg cgctcccttg ccagcccgtg atatgtggac gatggccgc    1020
gagcggccac cggctggctc gcttcgctcg gcccgtggac aaccctgctg acaagctga    1080
tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt ggggcagtc gaaggcgaag cccgcccgcc    1380
tgcccccga gacctgcagg gggggggggg cgctgaggtc tgcctcgtga agaaggtgtt    1440
gctgactcat accaggcctg aatcgcccca tcatccagcc agaaagtgag ggagccacgg    1500
ttgatgagag ctttgttgta ggtggaccag ttggtgattt tgaactttg ctttgccacg    1560
gaacggtctg cgttgtcggg aagatgcgtg atctgatcct tcaactcagc aaaagttcga    1620
tttattcaac aaagccgccg tcccgtcaag tcagcgtaat gctctgccag tgttacaacc    1680
aattaaccaa ttctgattag aaaaactcat cgagcatcaa atgaaactgc aatttattca    1740
tatcaggatt atcaatacca tattttgaa aaagccgttt ctgtaatgaa ggagaaaact    1800
caccgaggca gttccatagg atggcaagat cctggtatcg gtctgcgatt ccgactcgtc    1860
caacatcaat acaacctatt aatttcccct cgtcaaaaat aaggttatca agtgagaaat    1920
caccatgagt gacgactgaa tccggtgaga atggcaaaag cttatgcatt tctttccaga    1980
cttgttcaac aggccagcca ttacgctcgt catcaaaatc actcgcatca accaaaccgt    2040
tattcattcg tgattgcgcc tgagcgagac gaaatacgcg atcgctgtta aaaggacaat    2100
tacaaacagg aatcgaatgc aaccggcgca ggaacactgc cagcgcatca acaatatttt    2160
cacctgaatc aggatattct tctaatacct ggaatgctgt tttcccgggg atcgcagtgg    2220
tgagtaacca tgcatcatca ggagtacgga taaaatgctt gatggtcgga agaggcataa    2280
attccgtcag ccagtttagt ctgaccatct catctgtaac atcattggca acgctacctt    2340
tgccatgttt cagaaacaac tctggcgcat cgggcttccc atacaatcga tagattgtcg    2400
cacctgattg cccgacatta tcgcgagccc atttatatccc atataaatca gcatccatgt    2460
tggaatttaa tcgcggcctc gagcaagacg tttcccgttg aatatggctc ataacacccc    2520
ttgtattact gtttatgtaa gcagacagtt ttattgttca tgatgatata ttttatctt    2580
gtgcaatgta acatcagaga ttttgagaca caacgtggct ttcccccccc ccctgcagg    2640
tcccgagcct cacggcggcg agtgcggggg ttccaagggg gcagcgccac cttgggcaag    2700
gccgaaggcc gcgcagtcga tcaacaagcc ccggagggggc cacttttgc cggaggggga    2760
gccgcgccga aggcgtgggg gaaccccgca gggtgccct tctttgggca ccaaagaact    2820
agatataggg cgaaatgcga aagcttaaa aatcaacaac ttaaaaaagg ggggtacgca    2880
acagctcatt gcggcacccc ccgcaatagc tcattgcgta ggttaaagaa atctgtaat    2940
tgactgccac ttttacgcaa cgcataattg ttgtcgcgct gccgaaaagt tgcagctgat    3000
tgcgcatggt gccgcaaccg tgcggcaccc taccgcatgg agataagc atg gcc acg    3057
                                                         Met Ala Thr
                                                           1
cag tcc aga gaa atc ggc att caa gcc aag aac aag ccc ggt cac tgg    3105
Gln Ser Arg Glu Ile Gly Ile Gln Ala Lys Asn Lys Pro Gly His Trp
```

```
              5                   10                  15
gtg caa acg gaa cgc aaa gcg cat gag gcg tgg gcc ggg ctt att gcg              3153
Val Gln Thr Glu Arg Lys Ala His Glu Ala Trp Ala Gly Leu Ile Ala
 20              25                  30                  35 agg aaa ccc acg gcg gca atg ctg ctg cat cac ctc gtg gcg cag atg              3201
Arg Lys Pro Thr Ala Ala Met Leu Leu His His Leu Val Ala Gln Met
                 40                  45                  50 ggc cac cag aac gcc gtg gtg gtc agc cag aag aca ctt tcc aag ctc              3249
Gly His Gln Asn Ala Val Val Val Ser Gln Lys Thr Leu Ser Lys Leu
                 55                  60                  65 atc gga cgt tct ttg cgg acg gtc caa tac gca gtc aag gac ttg gtg              3297
Ile Gly Arg Ser Leu Arg Thr Val Gln Tyr Ala Val Lys Asp Leu Val
             70                  75                  80 gcc gag cgc tgg atc tcc gtc gtg aag ctc aac ggc ccc ggc acc gtg              3345
Ala Glu Arg Trp Ile Ser Val Val Lys Leu Asn Gly Pro Gly Thr Val
         85                  90                  95 tcg gcc tac gtg gtc aat gac cgc gtg gcg tgg ggc cag ccc cgc gac              3393
Ser Ala Tyr Val Val Asn Asp Arg Val Ala Trp Gly Gln Pro Arg Asp
100                 105                 110                 115 cag ttg cgc ctg tcg gtg ttc agt gcc gcc gtg gtg gtt gat cac gac              3441
Gln Leu Arg Leu Ser Val Phe Ser Ala Ala Val Val Val Asp His Asp
                120                 125                 130 gac cag gac gaa tcg ctg ttg ggg cat ggc gac ctg cgc cgc atc ccg              3489
Asp Gln Asp Glu Ser Leu Leu Gly His Gly Asp Leu Arg Arg Ile Pro
                135                 140                 145 acc ctg tat ccg ggc gag cag caa cta ccg acc ggc ccc ggc gag gag              3537
Thr Leu Tyr Pro Gly Glu Gln Gln Leu Pro Thr Gly Pro Gly Glu Glu
            150                 155                 160 ccg ccc agc cag ccc ggc att ccg ggc atg gaa cca gac ctg cca gcc              3585
Pro Pro Ser Gln Pro Gly Ile Pro Gly Met Glu Pro Asp Leu Pro Ala
        165                 170                 175 ttg acc gaa acg gag gaa tgg gaa cgg cgc ggg cag cag cgc ctg ccg              3633
Leu Thr Glu Thr Glu Glu Trp Glu Arg Arg Gly Gln Gln Arg Leu Pro
180                 185                 190                 195 atg ccc gat gag ccg tgt ttt ctg gac gat ggc gag ccg ttg gag ccg              3681
Met Pro Asp Glu Pro Cys Phe Leu Asp Asp Gly Glu Pro Leu Glu Pro
                200                 205                 210 ccg aca cgg gtc acg ctg ccg cgc cgg tag cacttgggtt gcgcagcaac                3731
Pro Thr Arg Val Thr Leu Pro Arg Arg
                215                 220 ccgtaagtgc gctgttccag actatcggct gtagccgcct cgccgcccta taccttgtct            3791
gcctccccgc gttgcgtcgc ggtgcatgga gccgggccac ctcgacctga atggaagccg            3851
gcggcacctc gctaacggat tcaccgtttt tatcaggctc tgggaggcag aataaatgat            3911
catatcgtca attattacct ccacggggag agcctgagca aactggcctc aggcatttga            3971
gaagcacacg gtcacactgc ttccggtagt caataaaccg gtaaaccagc aatagacata            4031
agcggctatt taacgaccct gccctgaacc gacgaccggg tcgaatttgc tttcgaattt            4091
ctgccattca tccgcttatt atacttattc aggcgtagca ccaggcgttt aagggcacca            4151
ataactgcct aaaaaaatt acgccccgcc ctgccactca tcgcagtact gttgtaattc             4211
attaagcatt ctgccgacat ggaagccatc acagacggca tgatgaacct gaatcgccag            4271
cggcatcagc accttgtcgc cttgcgtata atatttgccc atggtgaaaa cggggcgaa             4331 gaagttgtcc atattggcca cgtttaaatc aaaactggtg aaactcaccc agggattggc            4391
tgagacgaaa aacatattct caataaaccc tttaggaaaa taggccaggt tttcaccgta            4451
acacgccaca tcttgcgaat atatgtgtag aaactgccgg aaatcgtcgt ggtattcact            4511
```

```
ccagagcgat gaaaacgttt cagtttgctc atggaaaacg gtgtaacaag ggtgaacact    4571
atcccatatc accagctcac cgtctttcat tgccatacgg aattccggat gagcattcat    4631
caggcgggca agaatgtgaa taaaggccgg ataaaacttg tgcttatttt tctttacggt    4691
ctttaaaaag gccgtaatat ccagctgaac ggtctggtta taggtacatt gagcaactga    4751
ctgaaatgcc tcaaaatgtt ctttacgatg ccattgggat atatcaacgg tggtatatcc    4811
agtgattttt ttctccattt tagcttcctt agctcctgaa atctcgata actcaaaaaa    4871 tacgcccggt agtgatctta tttcattatg gtgaaagttg gaacctctta cgtgccgatc    4931
aacgtctcat tttcgccaaa agttggccca gggcttcccg gtatcaacag ggacaccagg    4991
atttatttat tctgcgaagt gatcttccgt cacaggtatt tattcggcgc aaagggcctc    5051
gtgatacgcc tatttttata ggttaatgtc atgataataa tggtttctta gacgtcaggt    5111
ggcacttttc ggggaaatgt gcgcgcccgc gttcctgctg cgctgggcc tgtttctggc     5171 gctggacttc ccgctgttcc gtcagcagct tttcgcccac ggccttgatg atcgcggcgg    5231
ccttggcctg catatcccga ttcaacggcc ccagggcgtc cagaacgggc ttcaggcgct    5291
cccgaaggt                                                            5300
```

<210> SEQ ID NO 2
<211> LENGTH: 220
<212> TYPE: PRT
<213> ORGANISM: Escherichia coli (GenBank Accession No. Y14439)

<400> SEQUENCE: 2

```
Met Ala Thr Gln Ser Arg Glu Ile Gly Ile Gln Ala Lys Asn Lys Pro
1               5                   10                  15

Gly His Trp Val Gln Thr Glu Arg Lys Ala His Glu Ala Trp Ala Gly
            20                  25                  30

Leu Ile Ala Arg Lys Pro Thr Ala Ala Met Leu Leu His His Leu Val
        35                  40                  45

Ala Gln Met Gly His Gln Asn Ala Val Val Ser Gln Lys Thr Leu
    50                  55                  60

Ser Lys Leu Ile Gly Arg Ser Leu Arg Thr Val Gln Tyr Ala Val Lys
65                  70                  75                  80

Asp Leu Val Ala Glu Arg Trp Ile Ser Val Val Lys Leu Asn Gly Pro
                85                  90                  95

Gly Thr Val Ser Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Gln Asp Glu Ser Leu Leu Gly His Gly Asp Leu Arg
    130                 135                 140

Arg Ile Pro Thr Leu Tyr Pro Gly Glu Gln Leu Pro Thr Gly Pro
145                 150                 155                 160

Gly Glu Glu Pro Pro Ser Gln Pro Gly Ile Pro Gly Met Glu Pro Asp
                165                 170                 175

Leu Pro Ala Leu Thr Glu Thr Glu Glu Trp Glu Arg Arg Gly Gln Gln
            180                 185                 190

Arg Leu Pro Met Pro Asp Glu Pro Cys Phe Leu Asp Asp Gly Glu Pro
        195                 200                 205

Leu Glu Pro Pro Thr Arg Val Thr Leu Pro Arg Arg
    210                 215                 220
```

<210> SEQ ID NO 3
<211> LENGTH: 663
<212> TYPE: DNA
<213> ORGANISM: Artificial Sequence
<220> FEATURE:
<223> OTHER INFORMATION: mutant rep gene

<400> SEQUENCE: 3

| | | | | | |
|---|---|---|---|---|---|
| atggccacgc | agtccagaga | aatcggcatt | caagccaaga | caagcccgg | tcactgggtg | 60 |
| caaacggaac | gcaaagcgca | tgaggcgtgg | gccgggctta | ttgcgaggaa | acccacrgcg | 120 |
| gcaatgctgc | tgcatcacct | cgtggcgcag | atgggccacc | agaacgccgt | ggtggtcagc | 180 |
| cagaagacac | tttccaagct | catcggacgt | tctktgcgga | yggtccaata | cgcagtcaag | 240 |
| gacttggtgg | ccgagcgctg | gatctccgtc | gtgaagctca | acggcccgg | caccgygtyg | 300 |
| gcctacgtgg | tcaatgaccg | cgtggcgtgg | ggccagcccc | gcgaccagtt | gcgcctgtcg | 360 |
| gtgttcagtg | ccgccgtggt | ggttgatcac | gacgaccagg | acgaatcrct | gttggggcay | 420 |
| ggcgacctgc | gccgcatccc | gaccctgtat | ccgggcgagc | agcaactacc | gaccggcccc | 480 |
| ggcgaggagc | cgcccagcca | gcccggcatt | ccgggcatgg | arccagacct | gccagccttg | 540 |
| accgaaacgg | aggaayggga | acggcgcggg | cagcagcgcc | tgccgatgcc | cgmtgagccg | 600 |
| tgttttctgg | acgatggcga | gccgttggag | ccgccgacac | gggtcacgct | gccgcgccgg | 660 |
| tag | | | | | | 663 |

<210> SEQ ID NO 4
<211> LENGTH: 1289
<212> TYPE: DNA
<213> ORGANISM: Artificial Sequence
<220> FEATURE:
<223> OTHER INFORMATION: pDCQ318 replication control region

<400> SEQUENCE: 4

| | | | | | |
|---|---|---|---|---|---|
| ctcgagcaag | acgtttcccg | ttgaatatgg | ctcataacac | cccttgtatt | actgtttatg | 60 |
| taagcagaca | gttttattgt | tcatgatgat | atatttttat | cttgtgcaat | gtaacatcag | 120 |
| agattttgag | acacaacgtg | gctttccccc | cccccctgc | aggtcccgag | cctcacggcg | 180 |
| gcgagtgcgg | ggggttccaag | ggggcagcgc | caccttgggc | aaggccgaag | ccgcgcagt | 240 |
| cgatcaacaa | gccccggagg | ggccactttt | tgccggaggg | ggagccgcgc | cgaaggcgtg | 300 |
| ggggaacccc | gcaggggtgc | ccttctttgg | gcaccaaaga | actagatata | gggcgaaatg | 360 |
| cgaaagactt | aaaaatcaac | aacttaaaaa | aggggggtac | gcaacagctc | attgcggcac | 420 |
| cccccgcaat | agctcattgc | gtaggttaaa | gaaaatctgt | aattgactgc | cacttttacg | 480 |
| caacgcataa | ttgttgtcgc | gctgccgaaa | agttgcagct | gattgcgcat | ggtgccgcaa | 540 |
| ccgtgcggca | ccctaccgc | atggagataa | gcatggccac | gcagtccaga | gaaatcggca | 600 |
| ttcaagccaa | gaacaagccc | ggtcactggg | tgcaaacgga | acgcaaagcg | catgaggcgt | 660 |
| gggccgggct | tattgcgagg | aaacccacgg | cggcaatgct | gctgcatcac | ctcgtggcgc | 720 |
| agatgggcca | ccagaacgcc | gtggtggtca | gccagaagac | actttccaag | ctcatcggac | 780 |
| gttctttgcg | gacggtccaa | tacgcagtca | aggacttggt | ggccgagcgc | tggatctccg | 840 |
| tcgtgaagct | caacgccccc | ggcaccgtgt | cggcctacgt | ggtcaatgac | cgcgtggcgt | 900 |
| ggggccagcc | ccgcgaccag | ttgcgcctgt | cggtgttcag | tgccgccgtg | gtggttgatc | 960 |
| acgacgacca | ggacgaatcg | ctgttggggc | atggcgacct | cgccgcatc | ccgaccctgt | 1020 |
| atccgggcga | gcagcaacta | ccgaccggcc | ccggcgagga | gccgcccagc | cagcccggca | 1080 |

```
ttccgggcat ggaaccagac ctgccagcct tgaccgaaac ggaggaatgg gaacggcgcg    1140
ggcagcagcg cctgccgatg cccgatgagc cgtgttttct ggacgatggc gagccgttgg    1200
agccgccgac acgggtcacg ctgccgcgcc ggtagcactt gggttgcgca gcaacccgta    1260
agtgcgctgt tccagactat cggctgtag                                       1289
```

<210> SEQ ID NO 5
<211> LENGTH: 220
<212> TYPE: PRT
<213> ORGANISM: Artificial Sequence
<220> FEATURE:
<223> OTHER INFORMATION: Rep protein

<400> SEQUENCE: 5

```
Met Ala Thr Gln Ser Arg Glu Ile Gly Ile Gln Ala Lys Asn Lys Pro
1               5                   10                  15

Gly His Trp Val Gln Thr Glu Arg Lys Ala His Glu Ala Trp Ala Gly
            20                  25                  30

Leu Ile Ala Arg Lys Pro Thr Ala Ala Met Leu Leu His His Leu Val
        35                  40                  45

Ala Gln Met Gly His Gln Asn Ala Val Val Val Ser Gln Lys Thr Leu
    50                  55                  60

Ser Lys Leu Ile Gly Arg Ser Leu Arg Thr Val Gln Tyr Ala Val Lys
65                  70                  75                  80

Asp Leu Val Ala Glu Arg Trp Ile Ser Val Val Lys Leu Asn Gly Pro
                85                  90                  95

Gly Thr Val Ser Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Asp Gln Asp Glu Ser Leu Leu Gly His Gly Asp Leu Arg
    130                 135                 140

Arg Ile Pro Thr Leu Tyr Pro Gly Glu Gln Gln Leu Pro Thr Gly Pro
145                 150                 155                 160

Gly Glu Glu Pro Pro Ser Gln Pro Gly Ile Pro Gly Met Glu Pro Asp
                165                 170                 175

Leu Pro Ala Leu Thr Glu Thr Glu Glu Trp Arg Arg Gly Gln Gln
            180                 185                 190

Arg Leu Pro Met Pro Asp Glu Pro Cys Phe Leu Asp Asp Gly Glu Pro
        195                 200                 205

Leu Glu Pro Pro Thr Arg Val Thr Leu Pro Arg Arg
    210                 215                 220
```

<210> SEQ ID NO 6
<211> LENGTH: 1289
<212> TYPE: DNA
<213> ORGANISM: Artificial Sequence
<220> FEATURE:
<223> OTHER INFORMATION: pDCQ318M1  replication control region

<400> SEQUENCE: 6

```
ctcgagcaag acgtttcccg ttgaatatgg ctcataacac cccttgtatt actgtttatg     60
taagcagaca gttttattgt tcatgatgat atatttttat cttgtgcaat gtaacatcag    120
agattttgag acacaacgtg gctttccccc ccccccctgc aggtcccgag cctcacggcg    180
gcgagtgcgg gggttccaag ggggcagcgc caccttgggc aaggccgaag gccgcgcagt    240
```

-continued

```
cgatcaacaa gccccggagg ggccactttt tgccggaggg ggagccgcgc cgaaggcgtg    300
ggggaacccc gcagggtgc ccttctttgg gcaccaaaga actagatata gggcgaaatg     360
cgaaagactt aaaaatcaac aacttaaaaa aggggggtac gcaacagctc attgcggcac    420
cccccgcaat agctcattgc gtaggttaaa gaaaatctgt aattgactgc cacttttacg    480
caacgcataa ttgttgtcgc gctgccgaaa agttgcagct gattgcgcat ggtgccgcaa    540
ccgtgcggca cccctaccgc atggagataa gcatggccac gcagtccaga gaaatcggca    600
ttcaagccaa gaacaagccc ggtcactggg tgcaaacgga acgcaaagcg catgaggcgt    660
gggccgggct tattgcgagg aaacccacgg cggcaatgct gctgcatcac ctcgtggcgc    720
agatgggcca ccagaacgcc gtggtggtca gccagaagac actttccaag ctcatcggac    780
gttctgtgcg gacggtccaa tacgcagtca aggacttggt ggccgagcgc tggatctccg    840
tcgtgaagct caacggcccc ggcaccgcgt cggcctacgt ggtcaatgac cgcgtggcgt    900
ggggccagcc ccgcgaccag ttgcgcctgt cggtgttcag tgccgccgtg gtggttgatc    960
acgacgacca ggacgaatcg ctgttggggc atggcgacct cgccgcatc ccgaccctgt    1020
atccgggcga gcagcaacta ccgaccggcc ccggcgagga gccgcccagc cagcccggca    1080
ttccgggcat ggaaccagac ctgccagcct tgaccgaaac ggaggaatgg gaacggcgcg    1140
ggcagcagcg cctgccgatg cccgatgagc cgtgttttct ggacgatggc gagccgttgg    1200
agccgccgac acgggtcacg ctgccgcgcc ggtagcactt gggttgcgca gcaacccgta    1260
agtgcgctgt tccagactat cggctgtag                                     1289
```

<210> SEQ ID NO 7
<211> LENGTH: 220
<212> TYPE: PRT
<213> ORGANISM: Artificial Sequence
<220> FEATURE:
<223> OTHER INFORMATION: Mutant Rep protein

<400> SEQUENCE: 7

```
Met Ala Thr Gln Ser Arg Glu Ile Gly Ile Gln Ala Lys Asn Lys Pro
1               5                   10                  15

Gly His Trp Val Gln Thr Glu Arg Lys Ala His Glu Ala Trp Ala Gly
            20                  25                  30

Leu Ile Ala Arg Lys Pro Thr Ala Ala Met Leu Leu His His Leu Val
        35                  40                  45

Ala Gln Met Gly His Gln Asn Ala Val Val Val Ser Gln Lys Thr Leu
    50                  55                  60

Ser Lys Leu Ile Gly Arg Ser Val Arg Thr Val Gln Tyr Ala Val Lys
65                  70                  75                  80

Asp Leu Val Ala Glu Arg Trp Ile Ser Val Val Lys Leu Asn Gly Pro
                85                  90                  95

Gly Thr Ala Ser Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Asp Gln Asp Glu Ser Leu Leu Gly His Gly Asp Leu Arg
    130                 135                 140

Arg Ile Pro Thr Leu Tyr Pro Gly Glu Gln Gln Leu Pro Thr Gly Pro
145                 150                 155                 160

Gly Glu Glu Pro Pro Ser Gln Pro Gly Ile Pro Gly Met Glu Pro Asp
                165                 170                 175
```

```
Leu Pro Ala Leu Thr Glu Thr Glu Trp Glu Arg Arg Gly Gln Gln
            180                 185                 190

Arg Leu Pro Met Pro Asp Glu Pro Cys Phe Leu Asp Asp Gly Glu Pro
        195                 200                 205

Leu Glu Pro Pro Thr Arg Val Thr Leu Pro Arg Arg
    210                 215                 220

<210> SEQ ID NO 8
<211> LENGTH: 1289
<212> TYPE: DNA
<213> ORGANISM: Artificial Sequence
<220> FEATURE:
<223> OTHER INFORMATION: pDCQ318M2   replication control region

<400> SEQUENCE: 8
ctcgagcaag acgtttcccg ttgaatatgg ctcataacac cccttgtatt actgtttatg      60
taagcagaca gttttattgt tcatgatgat atattttat  cttgtgcaat gtaacatcag     120
agattttgag acacaacgtg gctttcccc  cccccctgc  aggtcccgag cctcacggcg     180
gcgagtgcgg gggttccaag ggggcagcgc caccttgggc aaggccgaag gccgcgcagt     240
cgatcaacaa gccccggagg ggccactttt tgccggaggg ggagccgcgc cgaaggcgtg     300 ggggaaccc  gcaggggtgc ccttctttgg gcaccaaaga actagatata gggcgaaatg     360
cgaaagactt aaaaatcaac aacttaaaaa aggggggtac gcaacagctc attgcggcac     420
cccccgcaat agctcattgc gtaggttaaa gaaaatctgt aattgactgc cacttttacg     480
caacgcataa ttgttgtcgc gctgccgaaa agttgcagct gattgcgcat ggtgccgcaa     540
ccgtgcggca ccctaccgc  atggagataa gcatggccac gcagtccaga gaaatcggca     600
ttcaagccaa gaacaagccc ggtcactggg tgcaaacgga acgcaaagcg catgaggcgt     660
gggccgggct tattgcgagg aaacccacgg cggcaatgct gctgcatcac ctcgtggcgc     720
agatgggcca ccagaacgcc gtggtggtca gccagaagac actttccaag ctcatcggac     780
gttctttgcg gacggtccaa tacgcagtca aggacttggt ggccgagcgc tggatctccg     840
tcgtgaagct caacggcccc ggcaccgtgt tggcctacgt ggtcaatgac gcgtggcgt     900 ggggccagcc ccgcgaccag ttgcgcctgt cggtgttcag tgccgccgtg gtggttgatc     960
acgacgacca ggacgaatcg ctgttggggc atggcgacct cgccgcatc  ccgaccctgt    1020 atccgggcga gcagcaacta ccgaccggcc ccggcgagga gccgcccagc cagcccggca    1080
ttccgggcat ggaaccagac ctgccagcct tgaccgaaac ggaggaatgg gaacggcgcg    1140
ggcagcagcg cctgccgatg cccgatgagc cgtgttttct ggacgatggc gagccgttgg    1200
agccgccgac acgggtcacg ctgccgcgcc ggtagcactt gggttgcgca gcaacccgta    1260
agtgcgctgt tccagactat cggctgtag                                      1289

<210> SEQ ID NO 9
<211> LENGTH: 220
<212> TYPE: PRT
<213> ORGANISM: Artificial Sequence
<220> FEATURE:
<223> OTHER INFORMATION: Mutant Rep protein

<400> SEQUENCE: 9

Met Ala Thr Gln Ser Arg Glu Ile Gly Ile Gln Ala Lys Asn Lys Pro
1               5                   10                  15

Gly His Trp Val Gln Thr Glu Arg Lys Ala His Glu Ala Trp Ala Gly
            20                  25                  30
```

```
Leu Ile Ala Arg Lys Pro Thr Ala Ala Met Leu Leu His His Leu Val
        35                  40                  45

Ala Gln Met Gly His Gln Asn Ala Val Val Val Ser Gln Lys Thr Leu
 50                  55                  60

Ser Lys Leu Ile Gly Arg Ser Leu Arg Thr Val Gln Tyr Ala Val Lys
 65                  70                  75                  80

Asp Leu Val Ala Glu Arg Trp Ile Ser Val Val Lys Leu Asn Gly Pro
                 85                  90                  95

Gly Thr Val Leu Ala Tyr Val Val Asn Asp Arg Val Ala Trp Gly Gln
                100                 105                 110

Pro Arg Asp Gln Leu Arg Leu Ser Val Phe Ser Ala Ala Val Val Val
            115                 120                 125

Asp His Asp Asp Gln Asp Glu Ser Leu Leu Gly His Gly Asp Leu Arg
130                 135                 140

Arg Ile Pro Thr Leu Tyr Pro Gly Glu Gln Gln Leu Pro Thr Gly Pro
145                 150                 155                 160

Gly Glu Glu Pro Pro Ser Gln Pro Gly Ile Pro Gly Met Glu Pro Asp
                165                 170                 175

Leu Pro Ala Leu Thr Glu Thr Glu Glu Trp Arg Arg Gly Gln Gln
            180                 185                 190

Arg Leu Pro Met Pro Asp Glu Pro Cys Phe Leu Asp Asp Gly Glu Pro
            195                 200                 205

Leu Glu Pro Pro Thr Arg Val Thr Leu Pro Arg Arg
210                 215                 220

<210> SEQ ID NO 10
<211> LENGTH: 1288
<212> TYPE: DNA
<213> ORGANISM: Artificial Sequence
<220> FEATURE:
<223> OTHER INFORMATION: pDCQ318M3  replication control region

<400> SEQUENCE: 10
ctcgagcaag acgtttcctg ttgaatatgg ctcataacac cccttgtatt actgtttatg      60
taagcagaca gttttattgt tcatgatgat atatttttat cttgtgcaat gtaacatcag     120
agattttgag acacaacgtg gctttccccc ccccctgca ggtcccgagc ctcacggcgg     180
cgagtgcggg ggttccaagg gggcagcgcc accttgggca aggccgaagg ccgcgcagtc     240
gatcaacaag ccccggaggg gccacttttt gccggagggg gagccgcgcc gaaggcgtgg     300
gggaaccccg caggggtgcc cttcttcggg caccaaagaa ctagatatag ggcgaaatgc     360
gaaagactta aaaatcaaca acttaaaaaa gggggtacg caacagctca ttgcggcacc     420
ccccgcaata gctcattgcg taggttaaag aaaatctgta attgactgcc acttttacgc     480
aacgcataat tgttgtcgcg ctgccgaaaa gttgcagctg attgcgcatg gtgccgcaac     540
cgtgcggcac ccctaccgca tggagataag catggcacg cagtccagag aaatcggcat     600
tcaagccaag aacaagcccg gtcactgggt gcaaacggaa cgcaaagcgc atgaggcgtg     660
ggccgggctt attgcgagga aacccacggc ggcaatgctg ctgcatcacc tcgtggcgca     720
gatgggccac cagaacgccg tggtggtcag ccagaagaca cttttccaagc tcatcggacg     780 ttcttttgcgg atggtccaat acgcagtcaa ggacttggtg gccgagcgct ggatctccgt     840
cgtgaagctc aacggccccg gcaccgtgtc ggcctacgtg gtcaatgacc gcgtggcgtg     900
gggccagccc cgcgaccagt tgcgcctgtc ggtgttcagt gccgccgtgg tggttgatca     960
cgacgaccag gacgaatcgc tgttggggca tggcgacctg cgccgcatcc cgaccctgta    1020
```

```
tccgggcgag cagcaactac cgaccggccc cggcgaggag ccgcccagcc agcccggcat   1080
tccgggcatg aaccagacc tgccagcctt gaccgaaacg gaggaacggg aacggcgcgg    1140
gcagcagcgc ctgccgatgc ccgatgagcc gtgttttctg gacgatggcg agccgttgga   1200
gccgccgaca cgggtcacgc tgccgcgccg gtagcacttg ggttgcgcag caacccgtaa   1260
gtgcgctgtt ccagactatc ggctgtag                                      1288
```

<210> SEQ ID NO 11
<211> LENGTH: 220
<212> TYPE: PRT
<213> ORGANISM: Artificial Sequence
<220> FEATURE:
<223> OTHER INFORMATION: Mutant Rep protein

<400> SEQUENCE: 11

```
Met Ala Thr Gln Ser Arg Glu Ile Gly Ile Gln Ala Lys Asn Lys Pro
 1               5                  10                  15

Gly His Trp Val Gln Thr Glu Arg Lys Ala His Glu Ala Trp Ala Gly
            20                  25                  30

Leu Ile Ala Arg Lys Pro Thr Ala Ala Met Leu Leu His His Leu Val
        35                  40                  45

Ala Gln Met Gly His Gln Asn Ala Val Val Ser Gln Lys Thr Leu
    50                  55                  60

Ser Lys Leu Ile Gly Arg Ser Leu Arg Met Val Gln Tyr Ala Val Lys
65                  70                  75                  80

Asp Leu Val Ala Glu Arg Trp Ile Ser Val Val Lys Leu Asn Gly Pro
                85                  90                  95

Gly Thr Val Ser Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Asp Gln Asp Glu Ser Leu Leu Gly His Gly Asp Leu Arg
    130                 135                 140

Arg Ile Pro Thr Leu Tyr Pro Gly Glu Gln Gln Leu Pro Thr Gly Pro
145                 150                 155                 160

Gly Glu Glu Pro Pro Ser Gln Pro Gly Ile Pro Gly Met Glu Pro Asp
                165                 170                 175

Leu Pro Ala Leu Thr Glu Thr Glu Arg Glu Arg Gly Gln Gln
            180                 185                 190

Arg Leu Pro Met Pro Asp Glu Pro Cys Phe Leu Asp Asp Gly Glu Pro
    195                 200                 205

Leu Glu Pro Pro Thr Arg Val Thr Leu Pro Arg Arg
    210                 215                 220
```

<210> SEQ ID NO 12
<211> LENGTH: 1289
<212> TYPE: DNA
<213> ORGANISM: Artificial Sequence
<220> FEATURE:
<223> OTHER INFORMATION: pDCQ318M4  replication control region

<400> SEQUENCE: 12

```
ctcgagcaag acgtttcccg ttgaatatgg ctcataacac cccttgtatt actgtttatg     60
taagcagaca gttttattgt tcatgatgat atattttat cttgtgcaat gtaacatcag     120
agattttgag acacaacgtg gctttccccc cccccctgc aggtcccgag cctcacggcg     180
```

```
gcgagcgcgg gggttccaag ggggcagcgc caccttgggc aaggccgaag gccgcgcagt    240
cgatcaacaa gccccggagg ggccactttt tgccggaggg ggagccgcgc cgagggcgtg    300
ggggaacccc gcagggggtgc ccttctttgg gcaccaaaga actagatata gggcgaaatg   360
cgaaagactt aaaaatcaac aacttaaaaa aggggggtac gcaacagctc attgcggcac    420 ccccgcaat agctcattgc gtaggttaaa gaaaatctgt aattgactgc cacttttacg     480
caacgcataa ttgttgtcgc gctgccgaaa agttgcagct gattgtgcat ggtgccgcaa    540
ccgtgcggca ccctaccgc atggagataa gcatggccac gcagtccaga gaaatcggca     600
ttcaagccaa gaacaagccc ggtcactggg tgcaaacgga acgcaaagcg catgaggcgt    660
gggccgggct tattgcgagg aaacccacgg cggcaatgct gctgcatcac ctcgtggcgc    720
agatgggcca ccagaacgcc gtggtggtca gccagaagac actttccaag ctcatcggac    780
gttctttgcg gacggtccaa tacgcagtca aggacttggt ggccgagcgc tggatctccg    840
tcgtgaagct caacggcccc ggcaccgtgt cggcctacgt ggtcaatgac gcgtggcgt    900 ggggccagcc ccgcgaccag ttgcgcctgt cggtgttcag tgccgccgtg gtggttgatc    960
acgacgacca ggacgaatcg ctgttggggc atggcgacct cgccgcatc ccgaccctgt    1020 atccgggcga gcagcaacta ccgaccggcc ccggcgagga gccgcccagc cagcccggca    1080
ttccgggcat ggaaccagac ctgccagcct tgaccgaaac ggaggaatgg gaacggcgcg    1140
ggcagcagcg cctgccgatg cccgatgagc cgtgttttct ggacgatggc gagccgttgg    1200
agccgccgac acgggtcacg ctgccgcgcc ggtagcactt gggttgcgca gcaacccgta    1260
agtgcgctgt tccagactat cggctgtag                                     1289

<210> SEQ ID NO 13
<211> LENGTH: 1288
<212> TYPE: DNA
<213> ORGANISM: Artificial Sequence
<220> FEATURE:
<223> OTHER INFORMATION: pDCQ318M5  replication control region

<400> SEQUENCE: 13
ctcgagcaag acgtttcccg ttgaatatgg ctcataacac cccttgtatt actgtttatg     60
taagcagaca gttttattgt tcatgatgat atatttttat cttgtgcaat gtaacatcag    120
agattttgag acacaacgtg gctttccccc ccccctgca ggtcccgagc ctcacggcgg     180
cgagtgcggg ggttccaagg gggcagcgcc accttgggca aggccgaagg ccgcgcagtc    240
gatcaacaag ccccggaggg gccactttt gccgagggg gagccgcgcc gaaggcgtgg      300
gggaaccccg cagggggtgcc cttctttggg caccaaagaa ctagatatag ggcgaaatgc   360
gaaagactta aaaatcaaca acttaaaaaa gggggtacg caacagctca ttgcggcacc    420
ccccgcaata gctcattgcg taggttaaag aaaatctgta attgactgcc acttttacgc    480
aacgcataat tgttgtcgcg ctgccgaaaa gttgcagctg attgcgcatg gtgccgcaac    540
cgtgcggcac ccctaccgca tggagataag catggccacg cagtccagag aaatcggcat    600
tcaagccaag aacaagcccg gtcactgggt gcaaacggaa cgcaaagcgc atgaggcgtg    660 gccgggctt attgcgagga aacccacagc ggcaatgctg ctgcatcacc tcgtggcgca     720
gatgggccac cagaacgccg tggtggtcag ccagaagaca ctttccaagc tcatcggacg    780
ttctttgcgg acggtccaat acgcagtcaa ggacttggtg gccgagcgct ggatctccgt    840
cgtgaagctc aacggccccg gcaccgtgtt ggcctacgtg gtcaatgacc gcgtggcgtg    900 ggccagccc cgcgaccagt tgcgcctgtc ggtgttcagt gccgccgtgg tggttgatca    960
```

```
cgacgaccag gacgaatcgc tgttggggca tggcgacctg cgccgcatcc cgaccctgta    1020
tccgggcgag cagcaactac cgaccggccc cggcgaggag ccgcccagcc agcccggcat    1080
tccgggcatg gaaccagacc tgccagcctt gaccgaaacg gaggaatggg aacggcgcgg    1140
gcagcagcgc ctgccgatgc ccgatgagcc gtgttttctg gacgatggcg agccgttgga    1200
gccgccgaca cgggtcacgc tgccgcgccg gtagcacttg ggttgcgcag caacccgtaa    1260
gtgcgctgtt ccagactatc ggctgtag                                      1288
```

<210> SEQ ID NO 14
<211> LENGTH: 220
<212> TYPE: PRT
<213> ORGANISM: Artificial Sequence
<220> FEATURE:
<223> OTHER INFORMATION: Mutant Rep protein

<400> SEQUENCE: 14

```
Met Ala Thr Gln Ser Arg Glu Ile Gly Ile Gln Ala Lys Asn Lys Pro
1               5                   10                  15

Gly His Trp Val Gln Thr Glu Arg Lys Ala His Glu Ala Trp Ala Gly
            20                  25                  30

Leu Ile Ala Arg Lys Pro Thr Ala Ala Met Leu Leu His His Leu Val
        35                  40                  45

Ala Gln Met Gly His Gln Asn Ala Val Val Val Ser Gln Lys Thr Leu
    50                  55                  60

Ser Lys Leu Ile Gly Arg Ser Leu Arg Thr Val Gln Tyr Ala Val Lys
65                  70                  75                  80

Asp Leu Val Ala Glu Arg Trp Ile Ser Val Val Lys Leu Asn Gly Pro
                85                  90                  95

Gly Thr Val Leu Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Asp Gln Asp Glu Ser Leu Leu Gly His Gly Asp Leu Arg
    130                 135                 140

Arg Ile Pro Thr Leu Tyr Pro Gly Glu Gln Gln Leu Pro Thr Gly Pro
145                 150                 155                 160

Gly Glu Glu Pro Pro Ser Gln Pro Gly Ile Pro Gly Met Glu Pro Asp
                165                 170                 175

Leu Pro Ala Leu Thr Glu Thr Glu Glu Trp Glu Arg Arg Gly Gln Gln
            180                 185                 190

Arg Leu Pro Met Pro Asp Glu Pro Cys Phe Leu Asp Asp Gly Glu Pro
        195                 200                 205

Leu Glu Pro Pro Thr Arg Val Thr Leu Pro Arg Arg
    210                 215                 220
```

<210> SEQ ID NO 15
<211> LENGTH: 1287
<212> TYPE: DNA
<213> ORGANISM: Artificial Sequence
<220> FEATURE:
<223> OTHER INFORMATION: pDCQ318M7 replication control region

<400> SEQUENCE: 15

```
ctcgagcaag acgtttcccg ttgaatatgg ctcataacac cccttgtatt actgtttatg     60
taagcagaca gttttattgt tcatgatgat atattttat cttgtgcaat gtaacatcag     120
```

```
agatttgag acacaacgtg gcttcccccc cccctgcag gtcccgagcc tcacggcggc    180
gagtgcgggg gttccaaggg ggcagcgcca ccttgggcaa ggccgaaggc cgcgcagtcg    240
atcaacaagc cccggagggg ccacttttg ccggagggg agccgcgccg aaggcgtggg    300
ggaaccccgc agggtgccc ttctttgggc accaaagaac tagatatagg gcgaaatgcg    360
aaagacttaa aaatcaacaa cttaaaaag gggtacgc aacagctcat tgcggcaccc    420
cccgcaatag ctcattgcgt aggttaaaga aaatctgtaa ttgactgcca cttttacgca    480
acgcataatt gttgtcgcgc tgccgaaaag ttgcagctga ttgcgcatgg tgccgcaacc    540
gtgcggcacc cctaccgcat ggagataagc atggccacgc agtccagaga aatcggcatt    600
caagccaaga acaagcccgg tcactgggtg caaacggaac gcaaagcgca tgaggcgtgg    660
gccgggctta ttgcgaggaa acccacggcg gcaatgctgc tgcatcacct cgtggcgcag    720
atgggccacc agaacgccgt ggtggtcagc cagaagacac tttccaagct catcggacgt    780
tctttgcgga cggtccaata cgcagtcaag gacttggtgg ccgagcgctg gatctccgtc    840
gtgaagctca acggccccgg caccgtgttg gcctacgtgg tcaatgaccg cgtggcgtgg    900
ggccagcccc gcgaccagtt gcgcctgtcg gtgttcagtg ccgccgtggt ggttgatcac    960
gacgaccagg acgaatcgct gttggggcat ggcgacctgc gccgcatccc gaccctgtat    1020
ccgggcgagc agcaactacc gaccggcccc ggcgaggagc cgcccagcca gcccggcatt    1080
ccgggcatgg aaccagacct gccagccttg accgaaacgg aggaatggga acggcgcggg    1140
cagcagcgcc tgccgatgcc cgatgagccg tgttttctgg acgatggcga gccgttggag    1200
ccgccgacac gggtcacgct gccgcgccgg tagcacttgg gttgcgcagc gacccgtaag    1260
tgcgctgttc cagactatcg gctgtag                                          1287

<210> SEQ ID NO 16
<211> LENGTH: 220
<212> TYPE: PRT
<213> ORGANISM: Artificial Sequence
<220> FEATURE:
<223> OTHER INFORMATION: Mutant Rep protein

<400> SEQUENCE: 16

Met Ala Thr Gln Ser Arg Glu Ile Gly Ile Gln Ala Lys Asn Lys Pro
1               5                   10                  15

Gly His Trp Val Gln Thr Glu Arg Lys Ala His Glu Ala Trp Ala Gly
                20                  25                  30

Leu Ile Ala Arg Lys Pro Thr Ala Ala Met Leu Leu His His Leu Val
            35                  40                  45

Ala Gln Met Gly His Gln Asn Ala Val Val Ser Gln Lys Thr Leu
        50                  55                  60

Ser Lys Leu Ile Gly Arg Ser Leu Arg Thr Val Gln Tyr Ala Val Lys
65                  70                  75                  80

Asp Leu Val Ala Glu Arg Trp Ile Ser Val Lys Leu Asn Gly Pro
                85                  90                  95

Gly Thr Val Leu Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Asp Gln Asp Glu Ser Leu Leu Gly His Gly Asp Leu Arg
    130                 135                 140

Arg Ile Pro Thr Leu Tyr Pro Gly Glu Gln Gln Leu Pro Thr Gly Pro
145                 150                 155                 160
```

Gly Glu Glu Pro Pro Ser Gln Pro Gly Ile Pro Gly Met Glu Pro Asp
                165                 170                 175

Leu Pro Ala Leu Thr Glu Thr Glu Trp Glu Arg Arg Gly Gln Gln
            180                 185                 190

Arg Leu Pro Met Pro Asp Glu Pro Cys Phe Leu Asp Asp Gly Glu Pro
            195                 200                 205

Leu Glu Pro Pro Thr Arg Val Thr Leu Pro Arg Arg
        210                 215                 220

<210> SEQ ID NO 17
<211> LENGTH: 1289
<212> TYPE: DNA
<213> ORGANISM: Artificial Sequence
<220> FEATURE:
<223> OTHER INFORMATION: pDCQ318M8   replication control region

<400> SEQUENCE: 17
ctcgagcaag acgtttcccg ttgaatatgg ctcataacac cccttgtatt actgtttatg     60
taagcagaca gttttattgt tcatgatgat atatttttat cttgtgcaat gtaacatcag    120
agattttgag acacaacgtg ctttccccc ccccccctgc aggtcccgag cctcacggcg    180
gcgagtgcgg gggttccaag ggggcagcgc caccttgggc aaggccgaag ccgcgcagt    240 cgatcaacaa gccccggagg ggccactttt tgccggaggg ggagccgcgc cgaaggcgtg    300
gggaaccccc gcagggtgc ccttctttgg gcaccaaaga actagatata gggcgaaatg    360
cgaaagactt aaaaatcaac aacttaaaaa aggggggtac gcaacagctc attgcggcac    420
cccccgcaat agctcattgc gtaggttaaa gaaaatctgt aattgactgc cacttttacg    480
caacgcataa ttgttgtcgc gctgccgaaa agttgcagct gattgtgcat ggtgccgcaa    540
ccgtgcggca ccctaccgc atggagataa gcatggccac gcagtccaga gaaatcggca    600
ttcaagccaa gaacaagccc ggtcactggg tgcaaacgga acgcaaagcg catgaggcgt    660
gggccgggct tattgcgagg aaacccacgg cggcaatgct gctgcatcac ctcgtggcgc    720
agatgggcca ccagaacgcc gtggtggtca gccagaagac actttccaag ctcatcggac    780
gttctttgcg gacggtccaa tacgcagtca aggacttggt ggccgagcgc tggatctccg    840
tcgtgaagct caacgccccc ggcaccgtgt cggcctacgt ggtcaatgac gcgtggcgt    900 ggggccagcc ccgcgaccag ttgcgcctgt cggtgttcag tgccgccgtg gtggttgatc    960
acgacgacca ggacgaatcg ctgttggggc atggcgacct cgccgcatc ccgaccctgt   1020 atccgggcga gcagcaacta ccgaccggcc ccggcgagga gccgcccagc cagcccggca   1080
ttccgggcat ggaaccagac ctgccagcct tgaccgaaac ggaggaatgg gaacggcgcg   1140
ggcagcagcg cctgccgatg cccgatgagc cgtgttttct ggacgatggc gagccgttgg   1200
agccgccgac acgggtcacg ctgccgcgcc ggtagcactt gggttgcgca gcaacccgta   1260
agtgcgctgt tccagactat cggctgtag                                    1289

<210> SEQ ID NO 18
<211> LENGTH: 1289
<212> TYPE: DNA
<213> ORGANISM: Artificial Sequence
<220> FEATURE:
<223> OTHER INFORMATION: pDCQ318M14   replication control region

<400> SEQUENCE: 18
ctcgagcaag acgtttcccg ttgaatatgg ctcataacac cccttgtatt actgtttatg     60

```
taagcagaca gttttattgt tcatgatgat atatttttat cttgtgcaat gtaacatcag    120
agattttgag acacaacgtg gctttccccc cccccctgc aggtcccgag cctcacggcg    180
gcgagtgcgg gggttccaag ggggcagcgc caccttgggc aaggccgaag ccgcgcagt    240
cgatcaacaa gccccggagg ggccactttt tgccggaggg ggagccgcgc cgaaggcgtg    300
ggggaacccc gcagggggtgc ccttctttgg gcaccaaaga actagatata gggcgaaatg    360
cgaaagactt aaaaatcaac aacttaaaaa aggggggtac gcaacagctc attgcggcac    420
cccccgcaat agctcactgc gtaggttaaa gaaaatccgt aattgactgc cacttttacg    480
caacgcataa ttgttgtcgc gctgccgaaa agttgcagct gattgcgcat ggtgccgcaa    540
ccgtgcggca cccctaccgc atggagataa gcatggccac gcagtccaga gaaatcggca    600
ttcaagccaa gaacaagccc ggtcactggg tgcaaacgga acgcaaagcg catgaggcgt    660
gggccgggct tattgcgagg aaacccacgg cggcaatgct gctgcatcac ctcgtggcgc    720
agatgggcca ccagaacgcc gtggtggtca gccagaagac actttccaag ctcatcggac    780
gttctttgcg gacggtccaa tacgcagtca aggacttggt ggccgagcgc tggatctccg    840
tcgtgaagct caacggcccc ggcaccgtgt tggcctacgt ggtcaatgac cgcgtggcgt    900
ggggccagcc ccgcgaccag ttgcgcctgt cggtgttcag tgccgccgtg gtggttgatc    960
acgacgacca ggacgaatcg ctgttggggc atggcgacct cgccgcatc  ccgaccctgt   1020
atccgggcga gcagcaacta ccgaccggcc ccggcgagga gccgcccagc cagcccggca   1080
ttccgggcat ggagccagac ctgccagcct tgaccgaaac ggaggaatgg aacggcgcg    1140
ggcagcagcg cctgccgatg cccgctgagc cgtgttttct ggacgatggc gagccgttgg   1200
agccgccgac acgggtcacg ctgccgcgcc ggtagcactt gggttgcgca gcaacccgta   1260
agtgcgctgt tccagactat cggctgtag                                     1289
```

<210> SEQ ID NO 19
<211> LENGTH: 220
<212> TYPE: PRT
<213> ORGANISM: Artificial Sequence
<220> FEATURE:
<223> OTHER INFORMATION: Mutant Rep protein

<400> SEQUENCE: 19

```
Met Ala Thr Gln Ser Arg Glu Ile Gly Ile Gln Ala Lys Asn Lys Pro
 1               5                  10                  15

Gly His Trp Val Gln Thr Glu Arg Lys Ala His Glu Ala Trp Ala Gly
            20                  25                  30

Leu Ile Ala Arg Lys Pro Thr Ala Ala Met Leu Leu His His Leu Val
        35                  40                  45

Ala Gln Met Gly His Gln Asn Ala Val Val Val Ser Gln Lys Thr Leu
    50                  55                  60

Ser Lys Leu Ile Gly Arg Ser Leu Arg Thr Val Gln Tyr Ala Val Lys
65                  70                  75                  80

Asp Leu Val Ala Glu Arg Trp Ile Ser Val Val Lys Leu Asn Gly Pro
                85                  90                  95

Gly Thr Val Leu Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Asp Gln Asp Glu Ser Leu Leu Gly His Gly Asp Leu Arg
    130                 135                 140
```

```
Arg Ile Pro Thr Leu Tyr Pro Gly Glu Gln Gln Leu Pro Thr Gly Pro
145                 150                 155                 160

Gly Glu Glu Pro Pro Ser Gln Pro Gly Ile Pro Gly Met Glu Pro Asp
                165                 170                 175

Leu Pro Ala Leu Thr Glu Thr Glu Glu Trp Glu Arg Arg Gly Gln Gln
            180                 185                 190

Arg Leu Pro Met Pro Ala Glu Pro Cys Phe Leu Asp Asp Gly Glu Pro
        195                 200                 205

Leu Glu Pro Pro Thr Arg Val Thr Leu Pro Arg Arg
    210                 215                 220

<210> SEQ ID NO 20
<211> LENGTH: 1288
<212> TYPE: DNA
<213> ORGANISM: Artificial Sequence
<220> FEATURE:
<223> OTHER INFORMATION: pDCQ318M32   replication control region

<400> SEQUENCE: 20
ctcgagcaag acatttcccg ttgaatatgg ctcataacac cccttgtatt actgtttatg      60
taagcagaca gttttattgt tcatgatgat atatttttat cctgtgcaat gtaacatcag     120
agattttgag acacaacgtg gctttccccc cccccctgca ggtcccgagc ctcacggcgg     180
cgagtgcggg ggttccaagg gggcagcgcc accttgggca aggccgaagg ccgcgcagtc     240
gatcaacaag ccccggaggg gccactttt gccggagggg gagccgcgcc gaaggcgtgg      300
gggaaccccg caggggtgcc cttctttggg caccaaagaa ctagatatag ggcgaaatga     360
gaaagactta aaaatcaaca acttaaaaaa gggggtacg caacagctca ttgcggcacc      420
ccccgcaata gctcattgcg taggttaaag aaaatctgta attgactgcc acttttacgc     480
aacgcataat tgttgtcgcg ctgccgaaaa gttgcagctg attgtgcatg gtgccgcaac     540
cgtgcggcac ccctaccgca tggagataag catggccacg cagtccagag aaatcggcat     600
tcaagccaag aacaagcccg gtcactgggt gcaaacggaa cgcaaagcgc atgaggcgtg     660
ggccgggctt attgcgagga aacccacggc ggcaatgctg ctgcatcacc tcgtggcgca     720
gatgggccac cagaacgccg tggtggtcag ccagaagaca cttccaagc tcatcggacg      780
ttctttgcgg acggtccaat acgcagtcaa ggacttggtg ccgagcgct ggatctccgt      840
cgtgaagctc aacggccccg gcaccgtgtc ggcctacgtg gtcaatgacc gcgtggcgtg     900
gggccagccc cgcgaccagt tgcgcctgtc ggtgttcagt gccgccgtgg tggttgatca     960
cgacgaccag gacgaatcac tgttggggca tggcgacctg cgccgcatcc cgaccctgta    1020
tccgggcgag cagcaactac cgaccggccc cggcgaggag ccgcccagcc agcccggcat    1080
tccgggcatg gaaccagacc tgccagcctt gaccgaaacg gaggaatggg aacggcgcgg    1140
gcagcagcgc ctgccgatgc ccgatgagcc gtgttttctg gacgatggcg agccgttgga    1200
gccgccgaca cgggtcacgc tgccgcgccg gtagcacttg ggttgcgcag caacccgtaa    1260
gagcgctgtt ccagactatc ggctgtag                                       1288

<210> SEQ ID NO 21
<211> LENGTH: 1289
<212> TYPE: DNA
<213> ORGANISM: Artificial Sequence
<220> FEATURE:
<223> OTHER INFORMATION: pDCQ318M35   replication control region

<400> SEQUENCE: 21
```

```
ctcgagcaag acgtttcccg ttgaatatgg ctcataacac cccttgtatt actgtttatg    60
taagcagaca gttttattgt tcatgatgat atattttat cttgtgcaat gtaacatcag   120
agattttgag acacaacgtg gctttccccc cccccctgc aggtcccgag cctcacggcg    180
gcgagtgcgg gggttccaag ggggcagcgc caccttgggc aaggccgaag ccgcgcagt    240 cgatcaacaa gccccggagg ggccactttt tgccggaggg ggagccgcgc cgaaggcgtg    300
ggggaacccc gcagggtgc ccttctttgg gcaccaaaga actagatata gggcgaaatg    360
cgaaagactt aaaaatcaac aacttaaaaa aggggggtac gcaacagctc attgcggcac    420
cccccgcaat agctcattgc gtaggttaaa gaaaatctgt aattgactgc cacttttacg    480
caacgcataa ttgttgtcgc gctgccgaaa agttgcagct gattgtgcat ggtgccgcaa    540
ccgtgcggca ccctaccgc atggagataa gcatggccac gcagtccaga gaaatcggca    600
ttcaagccaa gaacaagccc ggtcactggg tgcaaacgga acgcaaagcg catgaggcgt    660
gggccgggct tattgcgagg aaacccacag cggcaatgct gctgcatcac ctcgtggcgc    720
agatgggcca ccagaacgcc gtggtggtca gccagaagac actttccaag ctcatcggac    780
gttctttgcg gacggtccaa tacgcagtca aggacttggt ggccgagcgc tggatctccg    840
tcgtgaagct caacggcccc ggcaccgtgt cggcctacgt ggtcaatgac cgcgtggcgt    900
ggggccagcc ccgcgaccag ttgcgcctgt cggtgttcag tgccgccgtg gtggttgatc    960
acgacgacca ggacgaatcg ctgttggggc acggcgacct gcgccgcatc ccgaccctgt   1020
atccgggcga gcagcaacta ccgaccggcc cggcgaggag gccgcccagc cagcccggca   1080
ttccgggcat ggaaccagac ctgccagcct tgaccgaaac ggaggaatgg gaacggcgcg   1140
ggcagcagcg cctgccgatg cccgatgagc cgtgttttct ggacgatggc gagccgttgg   1200
agccgccgac acgggtcacg ctgccgcgcc ggtagcactt gggttgcgca gcaacccgta   1260
agtgcgctgt cccagactat cggctgtag                                     1289

<210> SEQ ID NO 22
<211> LENGTH: 20
<212> TYPE: DNA
<213> ORGANISM: Artificial Sequence
<220> FEATURE:
<223> OTHER INFORMATION: Primer pBHRcrt_1F

<400> SEQUENCE: 22
gaattcgccc ttgacggtct                                                20

<210> SEQ ID NO 23
<211> LENGTH: 50
<212> TYPE: DNA
<213> ORGANISM: Artificial Sequence
<220> FEATURE:
<223> OTHER INFORMATION: Primer pBHRcrt_1R

<400> SEQUENCE: 23
cggttgcata atcctgccca ctcaattgtt aactgacggc agcgagtttt                50

<210> SEQ ID NO 24
<211> LENGTH: 50
<212> TYPE: DNA
<213> ORGANISM: Artificial Sequence
<220> FEATURE:
<223> OTHER INFORMATION: Primer pBHRcrt_2F

<400> SEQUENCE: 24
aaaactcgct gccgtcagtt aacaattgag tgggcaggat tatgcaaccg                50
```

<210> SEQ ID NO 25
<211> LENGTH: 25
<212> TYPE: DNA
<213> ORGANISM: Artificial Sequence
<220> FEATURE:
<223> OTHER INFORMATION: Primer pBHRcrt_2R

<400> SEQUENCE: 25
ggtacctaga tcgggcgctg ccaga 25

<210> SEQ ID NO 26
<211> LENGTH: 20
<212> TYPE: DNA
<213> ORGANISM: Artificial Sequence
<220> FEATURE:
<223> OTHER INFORMATION: Primer 301rep_F

<400> SEQUENCE: 26
agattgtcgc acctgattgc 20

<210> SEQ ID NO 27
<211> LENGTH: 38
<212> TYPE: DNA
<213> ORGANISM: Artificial Sequence
<220> FEATURE:
<223> OTHER INFORMATION: Primer 301rep_R

<400> SEQUENCE: 27
cggggtaccg aattctacag ccgatagtct ggaacagc 38

<210> SEQ ID NO 28
<211> LENGTH: 25
<212> TYPE: DNA
<213> ORGANISM: Artificial Sequence
<220> FEATURE:
<223> OTHER INFORMATION: Primer pBHR1rep_F

<400> SEQUENCE: 28
atcgatagat tgtcgcacct gattg 25

<210> SEQ ID NO 29
<211> LENGTH: 20
<212> TYPE: DNA
<213> ORGANISM: Artificial Sequence
<220> FEATURE:
<223> OTHER INFORMATION: Primer 301rep_R2

<400> SEQUENCE: 29
catccggtca ggcagttact 20

<210> SEQ ID NO 30
<211> LENGTH: 17
<212> TYPE: DNA
<213> ORGANISM: Artificial Sequence
<220> FEATURE:
<223> OTHER INFORMATION: Primer (Forward) for 3' crtE

<400> SEQUENCE: 30
ccgcgcctga gcctaat 17

<210> SEQ ID NO 31
<211> LENGTH: 22
<212> TYPE: DNA
<213> ORGANISM: Artificial Sequence
<220> FEATURE:

-continued

<223> OTHER INFORMATION: Primer (Reverse) for 3' crtE

<400> SEQUENCE: 31
cggcaaagac atcaatcagg at                                         22

<210> SEQ ID NO 32
<211> LENGTH: 17
<212> TYPE: DNA
<213> ORGANISM: Escherichia coli

<400> SEQUENCE: 32
ccagcagccg cggtaat                                               17

<210> SEQ ID NO 33
<211> LENGTH: 20
<212> TYPE: DNA
<213> ORGANISM: Escherichia coli

<400> SEQUENCE: 33
tgcgctttac gcccagtaat                                            20

<210> SEQ ID NO 34
<211> LENGTH: 1429
<212> TYPE: DNA
<213> ORGANISM: Methylomonas sp. 16a (ATCC PTA 2402)

<400> SEQUENCE: 34
cggtatgctt aacacatgca agtcgaacgc tgaagggtgc ttgcacctgg atgagtggcg      60
gacgggtgag taatgcatag gaatctgcct attagtgggg gataacgtgg ggaaactcac    120
gctaataccg catacgctct acggaggaaa gccggggacc ttcgggcctg cgctaatag    180
atgagcctat gtcggattag ctagttggtg gggtaaaggc ctaccaaggc gacgatccgt    240
agctggtctg agaggatgat cagccacact gggactgaga cacggcccag actcctacgg    300
gaggcagcag tggggaatat tggacaatgg gcgcaagcct gatccagcaa taccgcgtgt    360
gtgaagaagg cctgagggtt gtaaagcact tcaatgggga aggaacacct atcggttaat    420
acccggtaga ctgacattac ccatacaaga agcaccggct aactccgtgc cagcagccgc    480
ggtaatacgg agggtgcaag cgttaatcgg aattactggg cgtaaagcgt gcgtaggcgg    540
tttttaagt cagatgtgaa agccctgggc ttaacctggg aactgcatt gatactgggg    600
aactagagtt gagtagagga gagtggaatt tcaggtgtag cggtgaaatg cgtagagatc    660
tgaaggaaca ccagtggcga aggcggctct ctggactcaa actgacgctg aggtacgaaa    720
gcgtgggtag caaacaggat tagataccct ggtagtccac gccgtaaacg atgtcaacta    780
accgttgggt tcttaaagaa cttagtggtg gagctaacgt attaagttga ccgcctgggg    840
agtacggccg caaggctaaa actcaaatga attgacgggg gcccgcacaa gcggtggagc    900
atgtggttta attcgatgca acgcgaagaa ccttacctac ccttgacatc ctcggaactt    960
gtcagagatg acttggtgcc ttcgggaacc gagagacagg tgctgcatgg ctgtcgtcag   1020
ctcgtgtcgt gagatgttgg gttaagtccc gtaacgagcg caacccttat ccttagttgc   1080
cagcgcgtca tgcgggaac tctagggaga ctgccggtga taaaccggag gaaggtgggg   1140
acgacgtcaa gtcatcatgg cccttatggg tagggctaca cacgtgctac aatggtcggt   1200
acagagggtt gcgaactcgc gagagccagc caatcccaaa aagccgatcc tagtccggat   1260
tgcagtctgc aactcgactt gcatgaagtc ggaatcgcta gtaatcgcgg atcagaatgc   1320
cgcggtgaat acgttcccgg gccttgtaca caccgcccgt cacaccatgg gagtgggttg   1380
caaaagaagt aggtagttta accttcggga gggcgcttac cactttgtg    1429

<210> SEQ ID NO 35
<211> LENGTH: 2152
<212> TYPE: DNA
<213> ORGANISM: Artificial Sequence
<220> FEATURE:
<223> OTHER INFORMATION: pDCQ301 replication control region

<400> SEQUENCE: 35

```
ctcgagcaag acgtttcccg ttgaatatgg ctcataacac cccttgtatt actgtttatg      60
taagcagaca gttttattgt tcatgatgat atatttttat cttgtgcaat gtaacatcag     120
agattttgag acacaacgtg gctttccccc ccccccctgc aggtcccgag cctcacggcg     180
gcgagtgcgg gggttccaag ggggcagcgc caccttgggc aaggccgaag gccgcgcagt     240
cgatcaacaa gccccggagg ggccactttt tgcggagggg ggagccgcgc cgaaggcgtg     300
ggggaacccc gcaggggtgc ccttctttgg gcaccaaaga actagatata gggcgaaatg     360
cgaaagactt aaaaatcaac aacttaaaaa aggggggtac gcaacagctc attgcgcac      420
ccccccgcaat agctcattgc gtaggttaaa gaaaatctgt aattgactgc cacttttacg     480
caacgcataa ttgttgtcgc gctgccgaaa agttgcagct gattgcgcat ggtgccgcaa     540
ccgtgcggca ccctaccgca tggagataag catggccacg cagtccagag aaatcggcat     600
tcaagccaag aacaagcccg gtcactgggt gcaaacggaa cgcaaagcgc atgaggcgtg     660
ggccgggctt attgcgagga aacccacggc ggcaatgctg ctgcatcacc tcgtggcgca     720
gatgggccac cagaacgccg tggtggtcag ccagaagaca cttccaagc tcatcggacg     780
ttctttgcgg acggtccaat acgcagtcaa ggacttggtg gccgagcgct ggatctccgt     840
cgtgaagctc aacggccccg gcaccgtgtc ggcctacgtg gtcaatgacc gcgtggcgtg     900
gggccagccc cgcgaccagt tgcgcctgtc ggtgttcagt gccgccgtgg tggttgatca     960
cgacgaccag gacgaatcgc tgttggggca tggcgacctg cgccgcatcc cgaccctgta    1020
tccgggcgag cagcaactac cgaccggccc cggcgaggag ccgcccagcc agcccggcat    1080
tccgggcatg gaaccagacc tgccagcctt gaccgaaacg gaggaatggg aacggcgcgg    1140
gcagcagcgc ctgccgatgc ccgatgagcc gtgttttctg gacgatggcg agccgttgga    1200
gccgccgaca cgggtcacgc tgccgcgccg gtagcacttg ggttgcgcag caacccgtaa    1260
gtgcgctgtt ccagactatc ggctgtagcc gcctcgccgc cctataccctt gtctgcctcc    1320
ccgcgttgcg tcgcggtgca tggagccggg ccacctcgac ctgaatggaa gccggcggca    1380
cctcgctaac ggattcaccg ttttttatcag gctctgggag gcagaataaa tgatcatatc    1440
gtcaattatt acctccacgg ggagagcctg agcaaactgg cctcaggcat ttgagaagca    1500
cacggtcaca ctgcttccgg tagtcaataa accggtaaac cagcaataga cataagcggc    1560
tatttaacga ccctgccctg aaccgacgac cgggtcgaat ttgctttcga atttctgcca    1620
ttcatccgct tattatactt attcaggcgt agcaccaggc gtttaagggc accaataact    1680
gccttaaaaa aattacgccc cgccctgcca ctcatcgcag tactgttgta attcattaag    1740
cattctgccg acatggaagc catcacagac ggcatgatga acctgaatcg ccagcggcat    1800
cagcaccttg tcgccttgcg tataatatttt gcccatggtg aaaacggggg cgaagaagtt    1860
gtccatattg gccacgttta aatcaaaact ggtgaaactc acccaggat tggctgagac    1920
gaaaaacata ttctcaataa acccttaggg gaaataggcc aggttttcac cgtaacacgc    1980
```

```
cacatcttgc gaatatatgt gtagaaactg ccggaaatcg tcgtggtatt cactccagag    2040
cgatgaaaac gtttcagttt gctcatggaa aacggtgtaa caagggtgaa cactatccca    2100
tatcaccagc tcaccgtctt tcattgccat acggaattcg cccttaggta cc            2152
```

<210> SEQ ID NO 36
<211> LENGTH: 220
<212> TYPE: PRT
<213> ORGANISM: Artificial Sequence
<220> FEATURE:
<223> OTHER INFORMATION: Rep protein

<400> SEQUENCE: 36

```
Met Ala Thr Gln Ser Arg Glu Ile Gly Ile Gln Ala Lys Asn Lys Pro
1               5                   10                  15

Gly His Trp Val Gln Thr Glu Arg Lys Ala His Glu Ala Trp Ala Gly
            20                  25                  30

Leu Ile Ala Arg Lys Pro Thr Ala Ala Met Leu Leu His His Leu Val
        35                  40                  45

Ala Gln Met Gly His Gln Asn Ala Val Val Ser Gln Lys Thr Leu
 50                  55                  60

Ser Lys Leu Ile Gly Arg Ser Leu Arg Thr Val Gln Tyr Ala Val Lys
65                  70                  75                  80

Asp Leu Val Ala Glu Arg Trp Ile Ser Val Val Lys Leu Asn Gly Pro
                85                  90                  95

Gly Thr Val Ser Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Gln Asp Glu Ser Leu Leu Gly His Gly Asp Leu Arg
    130                 135                 140

Arg Ile Pro Thr Leu Tyr Pro Gly Glu Gln Gln Leu Pro Thr Gly Pro
145                 150                 155                 160

Gly Glu Glu Pro Pro Ser Gln Pro Gly Ile Pro Gly Met Glu Pro Asp
                165                 170                 175

Leu Pro Ala Leu Thr Glu Thr Glu Glu Trp Glu Arg Arg Gly Gln Gln
            180                 185                 190

Arg Leu Pro Met Pro Asp Glu Pro Cys Phe Leu Asp Asp Gly Glu Pro
        195                 200                 205

Leu Glu Pro Pro Thr Arg Val Thr Leu Pro Arg Arg
    210                 215                 220
```